United States Patent
Fearnot et al.

(10) Patent No.: US 10,945,825 B2
(45) Date of Patent: Mar. 16, 2021

(54) ANEURYSM STOP PRESSURE SYSTEM

(71) Applicant: Muffin Incorporated, West Lafayette, IN (US)

(72) Inventors: Neal E. Fearnot, West Lafayette, IN (US); Palle Munk Hansen, Bjaeverskov (DK)

(73) Assignee: Muffin Incorporated, West Lafayette, IN (US)

( * ) Notice: Subject to any disclaimer, the term of this patent is extended or adjusted under 35 U.S.C. 154(b) by 361 days.

(21) Appl. No.: 15/355,167

(22) Filed: Nov. 18, 2016

(65) Prior Publication Data

US 2017/0065401 A1 Mar. 9, 2017

Related U.S. Application Data

(63) Continuation of application No. PCT/US2015/031546, filed on May 19, 2015.
(Continued)

(51) Int. Cl.
*A61F 2/07* (2013.01)
*A61B 17/12* (2006.01)
(Continued)

(52) U.S. Cl.
CPC .......... *A61F 2/07* (2013.01); *A61B 17/12118* (2013.01); *A61B 17/12177* (2013.01);
(Continued)

(58) Field of Classification Search
CPC .......... A61F 2002/075; A61F 2002/077; A61F 2002/9665; A61F 2/962; A61F 2/966;
(Continued)

(56) References Cited

U.S. PATENT DOCUMENTS 6,221,084 B1 * 4/2001 Fleenor .............. A61B 17/0469
606/148
6,613,074 B1 * 9/2003 Mitelberg ........ A61B 17/12022
606/200
(Continued)

FOREIGN PATENT DOCUMENTS

| WO | WO 2007/051179 | 5/2007 | |
| WO | WO 2009/019664 A2 | 2/2009 | |
| WO | WO-2009019664 A2 * | 2/2009 | ....... A61B 17/12022 |

OTHER PUBLICATIONS

Merriam-Webster Dictonary, definition of "rotate", 2009, www.merriam-webster.com/dictionary/rotate (Year: 2009).*
(Continued)

*Primary Examiner* — Eric J Rosen
*Assistant Examiner* — Mikail A Mannan
(74) *Attorney, Agent, or Firm* — Woodard, Emhardt, Henry, Reeves & Wagner, LLP

(57) ABSTRACT

Intravascular devices and systems useful for blocking the opening of an aneurysm or a vessel branch are disclosed. In some aspects, the disclosure provides arrangements that align a covering material of a stent graft with an opening in the vessel wall before, during, and/or after expansion of the stent graft within the vasculature of a patient. In some instances, systems and devices include a sheath with a side aperture arranged to align a portion of the sheath and/or a portion of a stent graft contained within the sheath with the mouth of an aneurysm. Similarly, the present disclosure also provides embodiments in which the stent graft comprises an aligning member arranged to align the stent graft and/or a sheath with the mouth of an aneurysm. Other embodiments are disclosed.

17 Claims, 15 Drawing Sheets

Related U.S. Application Data

(60) Provisional application No. 62/000,819, filed on May 20, 2014.

(51) Int. Cl.

| | | |
|---|---|---|
| A61F 2/966 | (2013.01) | |
| A61B 17/00 | (2006.01) | |
| A61B 90/00 | (2016.01) | |
| A61F 2/97 | (2013.01) | |
| A61F 2/82 | (2013.01) | |
| A61B 17/22 | (2006.01) | |
| A61F 2/90 | (2013.01) | |
| A61F 2/86 | (2013.01) | |
| A61F 2/856 | (2013.01) | |

(52) U.S. Cl.
CPC ..... *A61B 90/08* (2016.02); *A61B 2017/00455* (2013.01); *A61B 2017/00526* (2013.01); *A61B 2017/1205* (2013.01); *A61B 2017/22038* (2013.01); *A61B 2090/0811* (2016.02); *A61F 2/856* (2013.01); *A61F 2/86* (2013.01); *A61F 2/90* (2013.01); *A61F 2/966* (2013.01); *A61F 2/97* (2013.01); *A61F 2002/075* (2013.01); *A61F 2002/077* (2013.01); *A61F 2002/823* (2013.01); *A61F 2002/9665* (2013.01); *A61F 2230/0023* (2013.01); *A61F 2230/0026* (2013.01); *A61F 2230/0058* (2013.01); *A61F 2230/0078* (2013.01); *A61F 2240/001* (2013.01)

(58) Field of Classification Search
CPC ........ A61F 2/97; A61F 2/90; A61F 2002/823; A61F 2/856; A61F 2/07; A61F 2/95; A61F 2/954; A61B 2017/00455; A61B 2017/1205; A61B 17/12168; A61B 17/12177; A61B 17/12118; A61M 2025/0177; A61M 2025/018; A61M 2025/0183; A61M 2025/0186; A61M 2025/0188; A61M 25/01; A61M 25/0169; A61M 25/0172; A61M 25/007; A61M 25/10; A61M 2025/1052; A61M 2025/105; A61M 29/02; A61M 25/1002; A61M 25/104; A61M 25/1011; A61M 25/0108; A61M 2025/1061; A61M 31/002; A61M 2025/0042; A61M 2025/1079; A61M 25/0074; A61M 25/10184; A61M 5/00; A61M 2025/0681; A61M 2025/1084; A61M 2025/0026; A61M 1/3659; A61M 2025/0004; A61M 2025/0079; A61M 2025/1047; A61M 25/00; A61M 25/0023; A61M 25/0052; A61M 25/0067; A61M 25/1034; A61M 2210/125; A61M 2210/1433; A61M 25/003; A61M 25/0043; A61M 25/0054; A61M 25/0082; A61M 2025/1031; A61M 2039/062

See application file for complete search history.

(56) References Cited

U.S. PATENT DOCUMENTS

| | | | |
|---|---|---|---|
| 8,961,532 B2 * | 2/2015 | Tremulis | A61M 25/0068 606/108 |
| 2002/0169473 A1 | 11/2002 | Sepetka et al. | |
| 2003/0120213 A1 * | 6/2003 | Nash | A61M 25/00 604/160 |
| 2003/0139752 A1 * | 7/2003 | Pasricha | A61B 17/0469 606/139 |
| 2003/0171801 A1 | 9/2003 | Bates | |
| 2006/0287712 A1 * | 12/2006 | Eidenschink | A61F 2/856 623/1.35 |
| 2007/0050008 A1 | 3/2007 | Kim et al. | |
| 2007/0078504 A1 * | 4/2007 | Mialhe | A61B 17/0057 623/1.11 |
| 2007/0100430 A1 | 5/2007 | Rudakov et al. | |
| 2007/0191884 A1 | 8/2007 | Eskridge et al. | |
| 2007/0233220 A1 | 10/2007 | Greenan | |
| 2008/0065141 A1 * | 3/2008 | Holman | A61F 2/954 606/194 |
| 2008/0114436 A1 * | 5/2008 | Dieck | A61F 2/86 623/1.11 |
| 2009/0069880 A1 * | 3/2009 | Vonderwalde | A61B 17/12022 623/1.13 |
| 2009/0270974 A1 * | 10/2009 | Berez | A61F 2/844 623/1.17 |
| 2010/0063531 A1 * | 3/2010 | Rudakov | A61B 17/12022 606/194 |
| 2010/0160949 A1 | 6/2010 | Takuma | |
| 2011/0022149 A1 | 1/2011 | Cox et al. | |
| 2011/0152993 A1 | 6/2011 | Marchand et al. | |
| 2011/0160833 A1 * | 6/2011 | Gonzalez | A61F 2/07 623/1.11 |
| 2012/0290069 A1 * | 11/2012 | Ivancev | A61F 2/07 623/1.13 |
| 2013/0218259 A1 * | 8/2013 | Quinn | A61F 2/07 623/1.16 |
| 2013/0297007 A1 * | 11/2013 | Kuchela | A61M 25/0662 623/1.23 |
| 2015/0080945 A1 * | 3/2015 | Michalak | A61B 17/0057 606/213 |
| 2015/0272754 A1 * | 10/2015 | Kavteladze | A61F 2/95 623/1.11 |

OTHER PUBLICATIONS

"Conditions & Diseases: Cardiovascular System", OmniMedical Search.com, www.omnimedicalsearch.com/conditions-diseases/aneurysm-types.html.

"Types of Aneurysms", Johns Hopkins Medicine, www.hopkinsmedicine.org/neurology_neurosurgery/speciality_areas/.../types/.

* cited by examiner

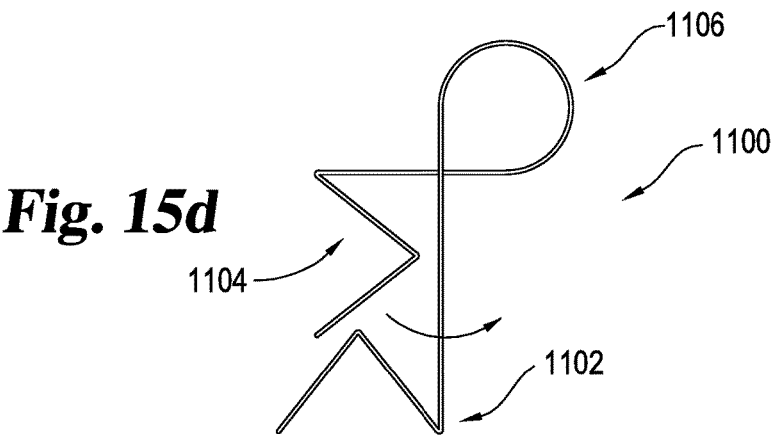
*Fig. 15d*
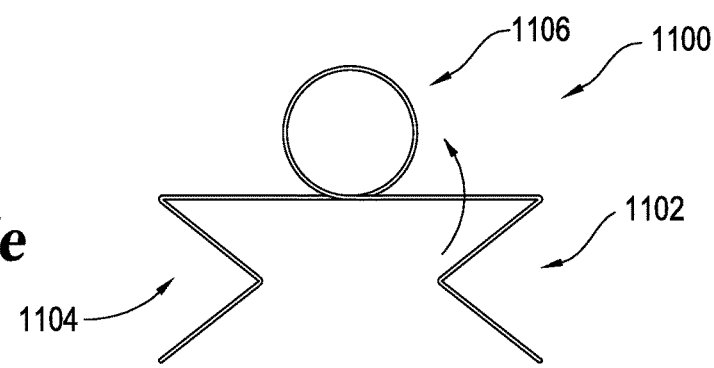
*Fig. 15e*
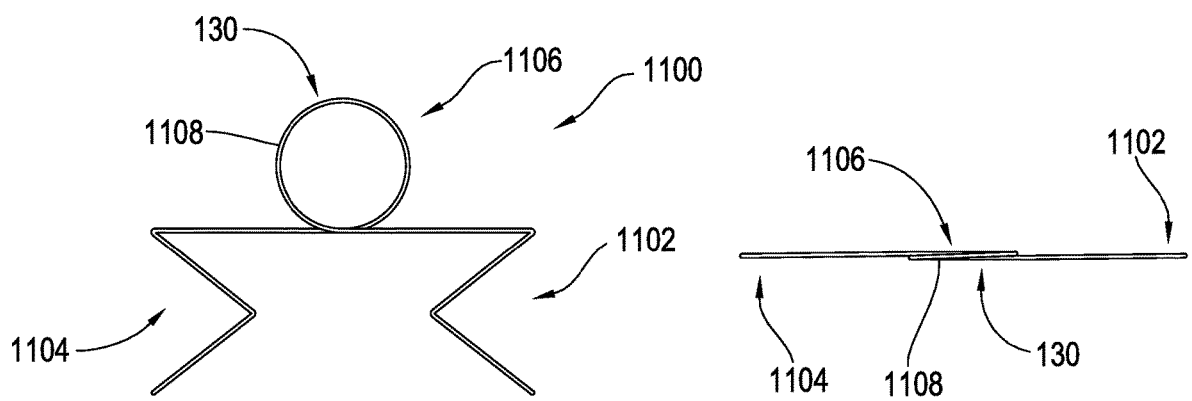
*Fig. 15f*  *Fig. 16*

ANEURYSM STOP PRESSURE SYSTEM

FIELD OF THE INVENTION

The present disclosure generally pertains to the field of implantable medical devices. More particularly, the present invention relates to closure devices and methods for blocking blood flow into an aneurysm.

BACKGROUND

Aneurysms are dilations that are caused from weakening of a blood vessel wall. The dilation is produced by the pressure exerted by blood flow, which causes the weakened segment of the blood vessel, such as an artery or vein, to expand. Aneurysms, including cerebral aneurysms, oftentimes occur in areas where there is a change in direction of blood flow, such as at a bifurcation of the vessel or at a bend in the vessel. The inertia of the moving blood can cause portions of the vessel wall to experience higher shear stress and can increase turbulent flow in the vessel. It is in these areas that aneurysms are more likely to form. In patients experiencing high blood pressure, the stress on the vessel wall is even greater as is the risk of an aneurysm being formed and rupturing.

In some types of aneurysms, such as intracranial aneurysms, this expansion may result in a balloon-like polyp (sometimes referred to as berry aneurysm). In other cases the expansion causes a circumscribed bulge in the blood vessel, as is the case with aortic aneurysms. Continued growth and/or eventual rupture of the ballooned arterial wall can have devastating results for patients. Consequently, unruptured aneurysms are usually treated to prevent hemorrhage, while ruptured aneurysms are typically treated to avert re-rupture and additional concomitant damage.

One surgical intervention for weakened, aneurysmal, or ruptured vessels involves the use of an endoluminal prosthesis such as a stent graft. Such a prosthesis may provide some or all of the functionality of the original, healthy vessel and/or preserve any remaining vascular integrity by replacing a length of the existing vessel wall that spans the site of vessel failure. A prosthesis of this type can treat, for example, aneurysms of the abdominal aortic, iliac, or renal arteries. For instance, a prosthesis may be used to span an aneurysm which has occurred in or is associated with an iliac artery.

In many cases, such a damaged or defective portion of the vasculature may include a branch vessel. For example, the celiac, superior mesenteric, left common carotid, and renal arteries are branch vessels of the aorta, and the internal iliac artery is a branch vessel of the common iliac artery. If the branch vessel is blocked by the prosthesis, the original blood circulation is impeded, and the patient can suffer. If, for example, the celiac artery is blocked by the prosthesis, the patient can experience abdominal pain, weight loss, nausea, bloating, and loose stools associated with mesenteric ischemia. The blockage of any branch vessel is usually associated with unpleasant or even life-threatening symptoms. Therefore devices suitable for blocking the mouth of the aneurysm while maintaining vessel patency of associated branch vessels are desired.

Graft-assemblies having partial covers and devices for delivering the same have been proposed; however, new graft devices and methods of deploying the same within the vasculature of a patient are desired.

SUMMARY

For the ease of the reader, the following disclosure has been described with reference to closing the opening or mouth of a berry aneurysm; however, it will be appreciated that the devices and methods disclosed herein may be used to block and/or occlude other types of aneurysms or openings in a vessel wall, such as an opening to a branch vessel. The present disclosure provides, in certain aspects, unique devices and methods for closing a mouth of an intracranial aneurysm; however, the disclosed devices and methods can be used to close the openings to aneurysms in other locations in the vasculature of a patient. In accordance with some forms of the disclosure, such devices and methods are arranged to orient a portion of an endoluminal prosthesis with the mouth of the aneurysm so as to not block an opening of an adjacent branch vessel.

In some embodiments, the system for delivering an endoluminal prosthesis comprises a delivery member, a stent graft, and an aligning member. The delivery member can comprise a sheath, such as an elongate sheath comprising a distal end region and a proximal end region with a sidewall extending there between. The sidewall of the sheath defines a lumen, and the lumen can be arranged to receive and/or retain the stent graft prior to deployment of the stent graft within the vasculature of the patient.

The sidewall of the sheath can also define a side aperture. The side aperture has a portion that is positioned proximally of said distal end region of the sheath and can be arranged to slidably receive a portion of the aligning member of the system. Alternatively or additionally, the side aperture can comprise a slot, such as an elongate slot, that extends along a length of the sheath. The slot extends from a distal slot end to a proximal slot end and can taper along a portion of or the entire length of the slot extending from the distal slot end to the proximal slot end, so that the tapered portion of the slot will direct a portion of a guide wire into the slot as the sheath is advanced over the guide wire. For example, portions of the sidewall of the sheath defining the slot may converge towards one another as the sidewall portions extend from the distal end region of the sheath towards the proximal end region of the sheath.

As will be appreciated, the sheath and/or portions thereof may be constructed of materials apparent to be suitable to those of ordinary skill in the art. For example, the sheath may be constructed of a nylon and/or a nylon wrapped stainless-steel braid, just to name a few non-limiting examples. Additionally, sheath may be provided with one or more coatings, such as a hydrophilic coating arranged to improve the ease with which the sheath may be advanced through the vasculature of the patient.

The stent graft of the system may comprise a supporting structure and a covering material. The supporting structure can be expandable between a first configuration and a second configuration. The first configuration can be arranged for positioning within the lumen of the sheath, such as to allow the compact delivery of the supporting structure to the target location within the vasculature of the patient. Accordingly, the second configuration of the supporting structure can be arranged for deployment within the vasculature. For example, the second configuration of the supporting structure may comprise an open and/or an expanded configuration in which the supporting structure of the stent graft presses one or more portions of the stent graft against the vessel wall. The supporting structure can also be arranged so as to have the same length in the first and second configurations which, advantageously, can help prevent misalignment of the covering material of the stent graft from the target aneurysm or opening in the vessel wall during expansion of the supporting structure.

The covering material of the stent graft can extend across a portion and/or the entire periphery of the supporting structure and can comprise one or more pieces and/or layers of material. For example, the covering material can extend along a length of the supporting structure and is sized and/or configured to close the mouth of an aneurysm. The covering material can define one or more openings, and these openings can be arranged to receive the aligning member and/or can comprise separable, overlapping portions of the covering material.

The covering material can be coupled to supporting structure in any number of ways. For example, portions of the covering material may be sutured to the supporting structure with one or more sutures; portions of the covering material may be wrapped around and/or sandwich portions of the supporting structure and the layers of the covering material bonded to one another such as by stitching, adhering with an adhesive, or heat bonding; and/or portions of the cover material may define apertures arranged to receive portions of the supporting structure or may be woven between members of the supporting structure such that the cover material has an intermediate section that is positioned on the inner or outer surface of a wall of the supporting structure and is positioned between sections of cover material on the opposing surface of the wall of the supporting structure. In some instances, the covering material comprises an electrospun fiber. Alternatively or additionally, the covering material can be made of a harvested tissue layer such as small intestinal submucosa, Dacron, nylon, expanded polytetrafluoroethylene (ePTFE), elastic membrane, or bioabsorbable materials such as poly-L-lactide (PLLA) or polylactic-co-glycolic acid (PLGA).

A stent graft comprising a covering material can be positioned on the delivery member in a predetermined alignment. For example, in some embodiments, the stent graft may be positioned within the lumen of the sheath with a covering material of the stent graft aligned with a side aperture or groove defined by the sidewall of the sheath so that when the side aperture or groove is aligned with a mouth of an aneurysm, the covering material is aligned with the mouth of the aneurysm as well. Alternatively or additionally, the covering material of the stent graft may be positioned in a predetermined alignment such that when a side aperture is aligned with the opening of a vessel branch, the cover material is aligned with the mouth of an adjacent aneurysm.

A side aperture or groove defined by the sidewall of the sheath is preferably arranged to receive the aligning member of the disclosed system. For example, in some instances, an aperture or groove is arranged to slidably receive the aligning. Alternatively or additionally, the side aperture and/or aligning member can be arranged so that the aligning member extends from the side aperture beyond the outer surface of the sidewall of the sheath such that a portion of the aligning member can enter and/or extend through the mouth of an aneurysm. Advantageously, in some instances, positioning a portion of the aligning member within the mouth of an aneurysm can align a portion of the stent graft with the mouth of the aneurysm.

An aligning member can be arranged to align at least a portion of the sheath with the mouth of an aneurysm. For example, an aligning member such as a wire guide may extend through a slot in the sidewall of the sheath and beyond the outer surface of the sheath and into a mouth of an aneurysm so that the interaction between the sides of the slot and the aligning member cause the slot of the sheath to rotate into alignment with mouth of the aneurysm and/or resist rotation of the sheath that would move the slot from an aligned position to an unaligned position.

The distal end region of the delivery member can be rotationally coupled and/or rotatable with respect to the proximal end region of the delivery member, so as to allow the distal end region to rotate independently of the proximal end region. Advantageously, this arrangement can allow automatic alignment of the distal end region of the stent graft when the aligning member is positioned within the mouth of the aneurysm. For example, for delivery systems in which the aligning member is a wire guide, the distal end region of the delivery member may be arranged to automatically rotate into an aligned configuration with the mouth of an aneurysm as the distal end region of the delivery member is advanced over the emplaced wire guide.

An aligning member can be arranged to align the stent graft with respect to the delivery member. For example, an aligning member coupled to the stent graft may be slidably received within an aperture or groove defined by the sidewall of the sheath so as to orient the covering material towards the aperture or groove or towards a particular side of the sheath. Additionally, the aperture or groove may extend along the length of the sheath so that the aligning member remains within the groove, and therefore the covering material remains in alignment with the sheath, as the stent graft is slidably advanced along a length of the sheath.

An aligning member can be arranged to align at least a portion of the stent graft with the mouth of the aneurysm. For example, the aligning member may be aligned with respect to the covering material of the stent graft so that when the aligning member extends into the mouth of an aneurysm, the covering material of the stent graft is aligned with the mouth of the aneurysm. Alternatively or additionally, an aligning member can be positioned with respect to the stent graft such that when the aligning member is positioned within the opening of a vessel branch, the covering material the stent graft is aligned with the mouth of an adjacent aneurysm or an adjacent branch vessel desired to be blocked.

In several embodiments, and aligning member and stent graft are coupled to one another. For example, an aligning member, such as a wire guide, can be slidably coupled to the stent graft so that the stent graft can slide along a length of the aligning member. Alternatively or additionally, an aligning member and a stent graft can be coupled so that the stent graft follows the aligning member during expansion of the supporting structure from a first configuration to a second configuration. It is also contemplated that an aligning member and stent graft can be coupled so that the aligning member resists rotational movement of the stent graft during expansion of the supporting structure from a first configuration to a second configuration and/or rotation of an expanded stent graft with respect to an adjacent vessel wall.

In instances in which the aligning member and stent graft are slidably coupled to one another, the aligning member can comprise a wire guide. For example, a wire guide can slidably extend through a lumen and/or through an opening of a stent graft, allowing the sheath and/or the stent graft to be advanced over a length of the wire guide towards the mouth of an aneurysm. Similarly, a slidable connection between an aligning member, such as a wire guide, and the stent graft can allow for the stent graft to slidably move along a length of the aligning member while a supporting structure of the stent graft expands from a first configuration to a second configuration.

In some embodiments, the aligning member and stent graft are fixedly coupled to one another with the aligning member arranged to extend away from the outer surface of the stent graft. In some instances, the aligning member is fixedly coupled to the supporting structure of the stent graft. Preferably, the aligning member comprises an opening engaging portion arranged to engage a side aperture of a sheath and/or an opening in a vessel wall. For example, the aligning member may comprise a wire configured to form an atraumatic loop configuration upon expansion, the loop configuration arranged to extend away from the outer surface of the supporting structure and into the mouth of an aneurysm. Additionally, the aligning member can be self-expanding and/or self-extending.

As will be appreciated, the aligning members and the supporting structure of the stent graft can comprise any material apparent to those of ordinary skill in the art to be suitable. For example, in certain embodiments, the aligning member is formed with a rigid or semi-rigid synthetic polymeric material, including but not limited to nylon, polytetrafluoroethylene (PTFE) (including expanded PTFE) and/or polyethylene terephthalate (PET). In other embodiments, an aligning member is formed with a rigid or semi-rigid metallic material, including but not limited to, stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Further in this regard, an aligning member can include a radiopaque material for positioning and monitoring the device within the vasculature of the patient.

In some instances, an aligning member can be integrally formed with a portion of the stent graft. For example, an aligning member may comprise a portion of the supporting structure of a stent graft bent into a loop configuration. Alternatively or additionally, an aligning member may be constructed as part of the stent graft during formation of the supporting structure. For example, during formation of a strut-based stent structure around a mandrel, a portion of the wire forming the stent structure may be bent into an atraumatic loop extending from the surface of the mandrel.

The coupling of the aligning member and the stent graft can be arranged to resist an undesirable movement of the stent graft, e.g., a rotation or translation, that may move a covering material of the stent graft out of alignment with a portion of the sheath or out of alignment with the mouth of the aneurysm and/or align a covering material with an opening of an adjacent vessel branch. The aligning member and the stent graft can be arranged to resist an undesirable movement of the stent graft before, during, and/or after expansion of the supporting structure. For example, the aligning member may align a covering material of the stent graft with the mouth of the aneurysm when the stent graft is in the first configuration and then resist rotation and/or translational movement of the stent graft during expansion of the supporting structure from the first configuration to the second configuration. Advantageously, the aligning member can be arranged to resist migration of the stent graft when the supporting structure is in the expanded configuration.

The aligning member and the stent graft can be arranged so that the stent graft follows the aligning member during expansion. For example, a portion of the aligning member, such as an aligning member distal tip, may be positioned within an aneurysm with a proximal portion of the aligning member slidably coupled with an opening defined by a covering material of a stent graft. As the supporting structure of the stent graft expands from a first configuration to a second configuration, the covering material slides along the aligning member, either moving into or maintaining alignment with the mouth of an aneurysm, so as to position the covering material over the mouth of the aneurysm. Preferably, the aligning member is arranged to prevent a misaligning movement of the stent graft within the vessel of the patient during expansion of the supporting structure.

In certain aspects, the present disclosure provides a system for delivering a stent graft useful for closing a mouth of an aneurysm in a vessel of a patient. The system comprises a delivery member, a stent graft, and an aligning member. The delivery member can comprise a sheath having a distal end region, a proximal end region, and a sidewall extending between the distal and proximal end regions. The sidewall defines a lumen extending along a length of the sheath and a side aperture extending through the sidewall and communicating with the lumen. The stent graft comprises a supporting structure and a covering material coupled to the supporting structure. The stent graft can be positioned within the lumen of a sheath-type delivery member or positioned along an outer surface of the delivery member (e.g., positioned around the delivery member). The supporting structure of the stent graft is expandable between a first configuration arranged for delivering the stent graft with the delivery member and a second configuration arranged for deployment in a vessel. The aligning member can be arranged for slidable receipt within the side aperture of the sheath and is coupled to the stent graft. The side aperture can have a portion positioned proximally of the distal end region of the sheath. Additionally or alternatively, the side aperture can comprise a slot that extends along a length of the sheath. The slot can be tapered along a length from a distal slot end to a proximal slot end. The aligning member can be arranged to extend from the side aperture beyond the sidewall of the sheath so as to enter the mouth of the aneurysm. The aligning member may also, or alternatively, be arranged to align at least a portion of the delivery member with the mouth of the aneurysm. In many instances, the aligning member is arranged to align the covering material of the stent graft with the mouth of the aneurysm. The aligning member can comprise a wire guide slidably coupled to the stent graft or can be fixedly coupled to the supporting structure of the stent graft.

The present disclosure also provides a stent graft useful for closing a mouth of an aneurysm. The stent graft comprises a supporting structure, a covering material, and an aligning member. The supporting structure is preferably expandable between a first configuration and a second configuration and defines a lumen in the second configuration. The supporting structure also has a covering material that extends along a length thereof and is sized and configured to close the mouth of the aneurysm. The aligning member is fixedly coupled to and arranged to extend away from the supporting structure. The aligning member can be arranged to extend away from the supporting structure when the supporting structure is in the first configuration. Alternatively or additionally, the aligning member can be arranged to extend away from the supporting structure and the lumen in the second configuration when the aligning member is aligned with an opening in a vessel wall adjacent to the stent graft. The aligning member can be arranged to prevent migration of the stent graft and/or can be arranged to align the stent graft with the mouth of the aneurysm prior to expansion of the supporting structure between the first and second configurations. The covering material can comprise an opening arranged to slidably receive a wire guide, and the opening can comprise separable, overlapping portions of the covering material.

The present disclosure also provides a device for deploying a stent within the vasculature of a patient, comprising a sheath having a distal end region, a proximal end region, and a sidewall extending between the distal and proximal end regions. The sidewall defines a lumen extending along a length of the sheath and a side aperture extending through the sidewall and communicating with the lumen. The side aperture has a portion positioned proximally of the distal end region of the sheath. The sheath is arranged to retain a stent for delivery within the vasculature of the patient; and the side aperture is arranged to slidably receive an aligning member. In some instances, the side aperture comprises a slot that extends along a length of the sheath. Additionally, the slot can comprise a taper along a length of the slot from a distal slot end to a proximal slot end. In many embodiments, the side aperture and/or the lumen is arranged to slidably receive an aligning member comprising a wire guide. In other instances, the side aperture can be arranged to slidably receive an aligning member that is fixedly coupled to the stent graft positioned within the lumen of the sheath.

In some arrangements, a system for delivering a stent graft useful for closing a mouth of an aneurysm in a vessel of a patient comprises both an aligning member slidably coupled to the stent graft and an aligning member fixedly coupled to or integrally formed with the stent graft. For example, the stent graft may be slidably coupled to a wire guide and have an atraumatic wire loop coupled to the supporting structure of the stent graft.

The systems of the present disclosure may also include one or more trigger wires that retain portions of the stent graft to the delivery member, such as a carrier member. The trigger wire(s) are arranged for selective operation so that one or more portions of the stent graft may be deployed from the stent graft delivery member. For example, the trigger wire(s) may extend to retain one or more end portions of the supporting structure to a carrier member by extending around a portion of the supporting structure and/or capturing a portion of the supporting structure between the trigger wire(s) and a surface of the carrier member.

Further forms, objects, features, aspects, benefits, advantages, and embodiments of the present invention will become apparent from a detailed description and drawings provided herewith.

BRIEF DESCRIPTION OF THE DRAWINGS

FIG. 7b illustrates a side, cross-sectional view of the embodiment of FIG. 7a.

FIG. 9b illustrates a top plan view of the embodiment illustrated in FIG. 9a.

FIG. 11b illustrates a top plan view of the embodiment illustrated in FIG. 11a.

FIG. 12b illustrates a top plan view of the embodiment illustrated in FIG. 12a.

FIGS. 15a, 15b, 15c, 15d, 15e and 15f illustrate a method of forming a supporting structure for an exemplary stent graft.

FIG. 16 illustrates a top plan view of the exemplary stent graft formed in FIGS. 15a-15f.

DESCRIPTION OF THE ILLUSTRATED EMBODIMENTS

Figure 1:
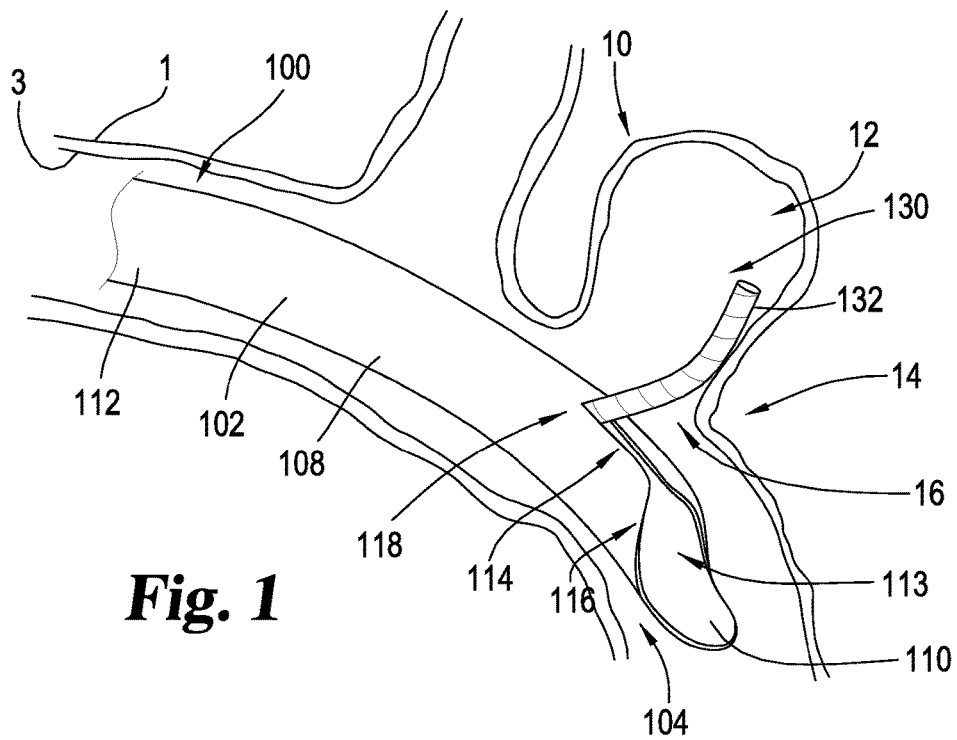
FIG. 1 illustrates a perspective view of a stent graft positioning device positioned within a vessel with an aneurysm.
Figure 2:
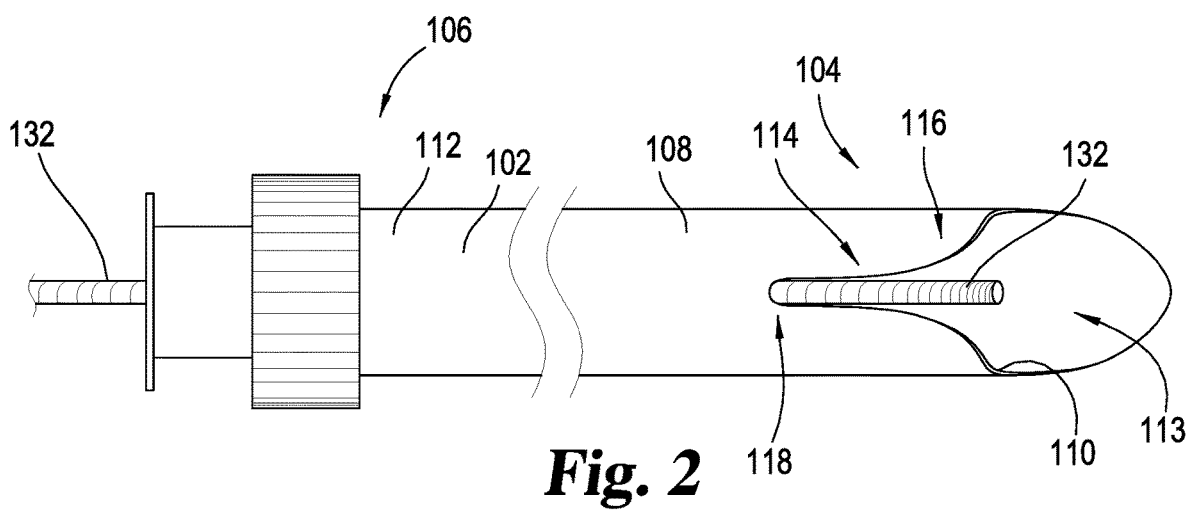
FIG. 2 illustrates a top plan view of the stent graft delivery device illustrated in FIG. 1.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The disclosed embodiments and variations thereof may be used to deliver at least one endoluminal prosthesis, such as a stent graft, to a location within the vasculature of a human and/or a veterinary patient. In particular, devices, systems, and methods for deploying a stent graft useful for closing a mouth of an aneurysm are disclosed. For simplicity, the following embodiments are discussed with reference to particular vessels in the body of a human patient; however, it is not intended that the present disclosure be limited to such.

FIG. 1 illustrates a stent graft delivery device 100 comprising a sheath 102 having a distal end region 104, a proximal end region 106 and a sidewall 108. Sidewall 108 defines a lumen 113 arranged to receive and retain a stent graft therein for advancement through a vessel 1 of a patient to a target location.

Device 100 may be arranged for positioning proximate an opening in a vessel wall 3, such as aneurysm 10, of a patient's vasculature. Openings such as aneurysm 10 can comprise an aneurismal sac 12, a neck 14 and a mouth 16. It should be appreciated that devices and methods of the present disclosure may be used to block the opening, such as mouth 16, of an aneurysm 10 with or without a neck 14.

Sidewall 108 of sheath 102 comprises an inner surface 110 and an outer surface 112. Inner surface 110 defines lumen 113 that extends along a length of sheath 102. Preferably, in some instances, sidewall 108 defines one or more side apertures, such as a slot 114, that communicate with lumen 113.

In some embodiments, slot 114 has a distal slot end 116 and a proximal slot end 118 and may taper along a length of slot 114, such as tapering from a wide configuration to a narrow configuration from distal slot end 116 towards proximal slot end 118.

In many instances, the side aperture defined by sidewall 108, such as slot 114, is arranged to receive an aligning member 130, such as a wire guide 132, arranged to align the sheath 102 with the aneurysm 10. For example, wire guide 132 may extend through the vasculature of the patient towards aneurysm 10 and the distal tip of wire guide 132 positioned within aneurismal sac 12. Sheath 102 may then be advanced over wire guide 132, with wire guide 132 slidably extending through lumen 113. As sheath 102 is advanced over wire guide 132, the slot 114 of sidewall 108 receives wire guide 132. As sheath 102 is advanced so as to positioned wire guide 132 near proximal slot end 118, the angle between wire guide 132 and the longitudinal axis of the distal end region 104 of sheath 102 increases, and sheath 102 rotates into an orientation in which slot 114 opens towards the mouth 16 of aneurysm 10. Advantageously, in some embodiments, sheath 102 will automatically rotate to align a side aperture, such as slot 114, with mouth 16 of aneurysm 10 as sheath 102 is advanced over wire guide 132.

Figure 3:
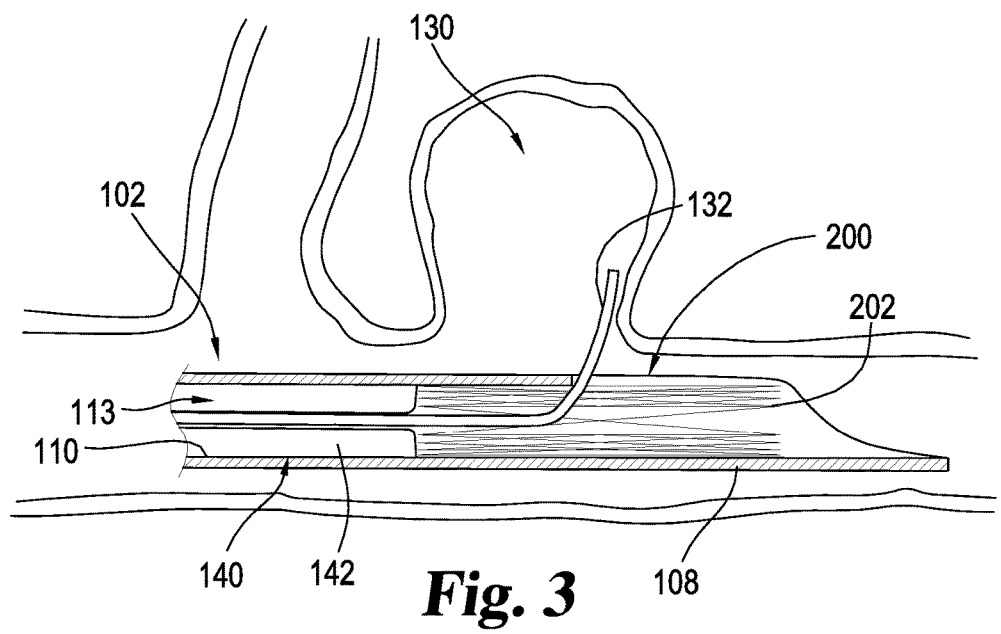
FIG. 3 illustrates a partial cross-sectional view of a stent graft delivery device.

Moving on to FIG. 3, device 100 can comprise a pushing member 140 arranged to push a stent graft 200 comprising at least a supporting structure 202 from within the lumen 113 defined by inner surface 110 of sidewall 108. Pushing member 140 comprises pushing portions 142 arranged to contact stent graft 200 and push stent graft 200 through and/or from lumen 113. Pushing member 140 may comprise a catheter that is slidably receivable within lumen 113 and advanced over wire guide 132. Alternatively, pushing member 140 may comprise pushing portions that are coupled to wire guide 132. The pushing member is arranged so that stent graft 200 may be pushed out of lumen 113 so as to expand from an initial configuration to a deployed, expanded configuration within the vasculature of the patient. The pushing member can also be arranged for pushing a stent graft through lumen 113 along the length of sheath 102.

Figure 4:
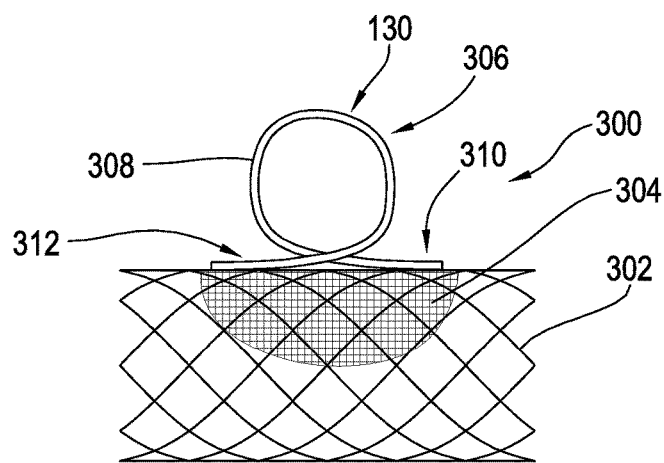
FIG. 4 illustrates a side-elevational view of an exemplary stent graft with an aligning member.
Figure 5:
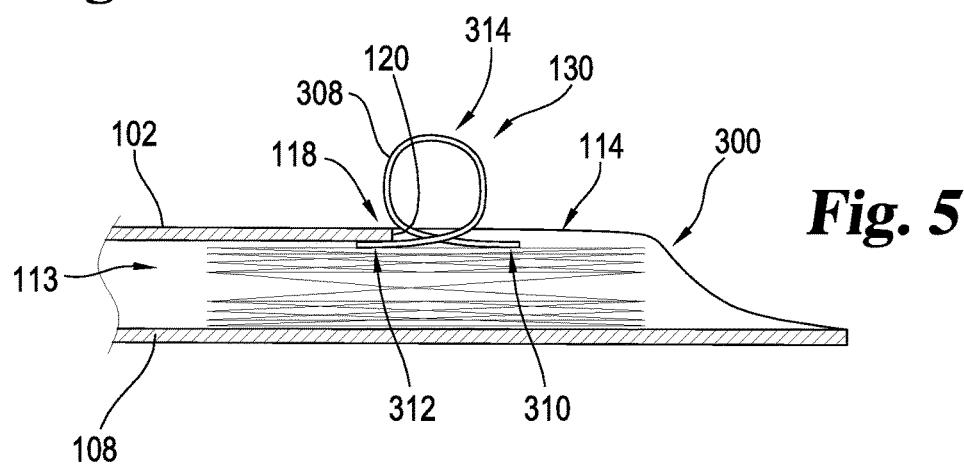
FIG. 5 illustrates the exemplary stent graft of FIG. 4 positioned within a delivery sheath.

FIGS. 4 and 5 illustrate another embodiment of a stent graft 300 comprising a supporting structure 302 and a covering material 304 extending across a surface of supporting structure 302. Stent graft 300 can also comprise an aligning member 130, such as loop 306. Loop 306 can be formed by a wire 308 having a distal portion 310, a proximal portion 312 and a central portion 314 extending between the distal portion 310 and proximal portion 312. Distal portion 310 and proximal portion 312 of wire 308 are fixedly coupled to supporting structure 302 of the stent graft 300, and central portion 314 forms an atraumatic loop 306 arranged for positioning within a portion of an aneurysm 10.

When stent graft 300 is positioned within lumen 113 of a sheath 102, aligning member 130, such as atraumatic loop 306, can extend from a side aperture such as slot 114 of sheath 102. Advantageously, aligning member 130 may be arranged for positioning within mouth 16 of aneurysm 10 so that a portion of stent graft 300 aligns with aneurysm 10 prior to deployment of stent graft 300 from within lumen 113 of sheath 102. For example, in embodiments in which atraumatic loop 306 is positioned over covering material 304, atraumatic loop will extend within mouth 16 of aneurysm 10 and align covering material 304 with mouth 16 so that when stent graft 300 is deployed, covering material 304 extends across and seals mouth 16.

As can be seen in FIG. 5, some arrangements are free of a pushing member 140. For example, sidewall 108 may have an edge 120 positioned at the proximal slot end 118. Edge 120 may be arranged to contact portions of an aligning member 130 such as atraumatic loop 306, so as to prevent stent graft 300 from migrating proximally within lumen 113 of sheath 102 during advancement of device 100 through the vasculature of a patient. In some instances, portions of sidewall 108 such as edge 120, wedge between the proximal portion 312 and central portion 314 of wire 308 so as to keep atraumatic loop 306 from collapsing and/or moving in a proximal direction. When stent graft 300 is in the desired position within the vasculature of the patient (i.e., when loop 306 is within the target aneurysm), stent graft 300 may be deployed by withdrawing sheath 102 in a proximal direction. Alternatively or additionally, a trigger wire and/or splittable sheath may be used to secure stent graft 300 to the distal end region of sheath 102 and removed or disconnected from stent graft 300 prior to or during deployment of stent graft 300.

Advantageously, aligning member 130, such as loop 306, can be arranged to extend into the mouth 16 of the aneurysm 10 when in alignment. For example, when loop 306 aligns with the mouth 16 of the aneurysm 10, loop 306 can extend, such as into the configuration illustrated in FIG. 5, into the aneurysm 10 and provide a tactile response (e.g., a greater resistance to movement in one or more directions) to indicate to the medical professional that loop 306 is aligned with an opening in the vessel wall. Alternatively or additionally, loop 306 may be visualized, such as by X-ray, so that a medical professional may see that loop 306 has extended into the aneurysm and is therefore aligning with an opening in the wall of the patient's vessel.

Figure 6:
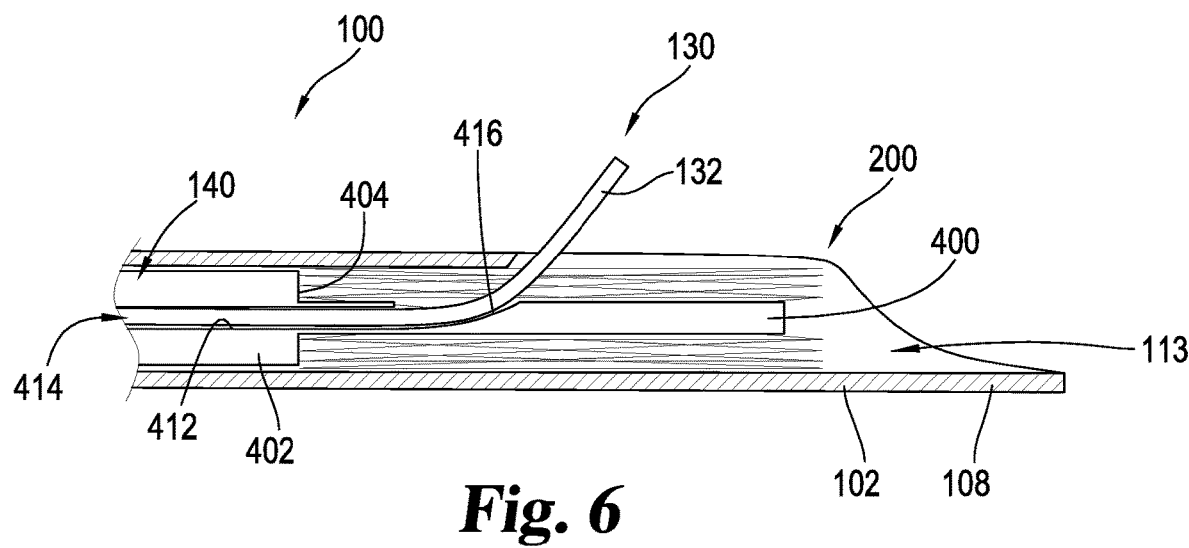
FIG. 6 illustrates another embodiment of a stent graft positioned within a delivery sheath with a wire guide extending therethrough.

FIG. 6 illustrates another embodiment of a device 100 having a stent graft 200 positioned within a lumen 113 of a sheath 102. As illustrated, the aligning member 130 can comprise a wire guide 132 that extends through lumen 113 and a side portion of stent graft 200. In some instances, device 100 further comprises a wire guide diverting member 400 positioned within lumen 113 of sheath 102. Wire guide diverting member 400 comprising a pusher 402 having a pushing surface 404 and an inner surface 412 that defines a lumen 414 for receiving wire guide 132. Wire guide diverting member 400 comprises an arcuate surface 416 arranged to divert portions of wire guide 132 through a side of stent graft 200. As discussed above, sheath 102 can be advanced over wire guide 132 until the side aperture is positioned adjacent the aneurysm, and stent graft 200 can be deployed from lumen 414 by pushing stent graft 200 with pusher 402, withdrawing sheath 102 from around stent graft 200, or a combination of pushing stent graft 200 with pusher 402 and withdrawing sheath 102.

Figure 7A:
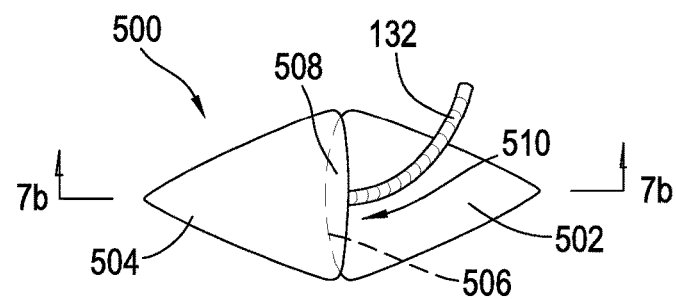
FIG. 7a illustrates a top plan view of a covering material of a stent graft.
Figure 7B:
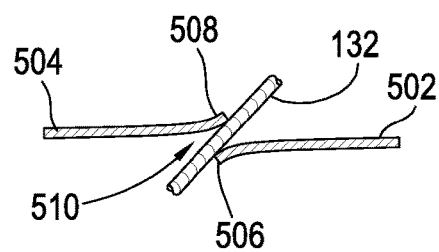

FIGS. 7a and 7b illustrate one arrangement of covering material 500 comprising a first portion 502 and second portion 504 overlapping along a seam so as to form an opening arranged to receive an aligning member 130, such as wire guide 132. For example, first portion 502 may comprise a first overlapping edge portion 506 that overlaps a second overlapping edge portion 508 of second portion 504. First overlapping edge portion 506 and second overlapping edge portion 508 cooperate to form a collapsible opening 510 arranged to receive wire guide 132.

Figure 8A:
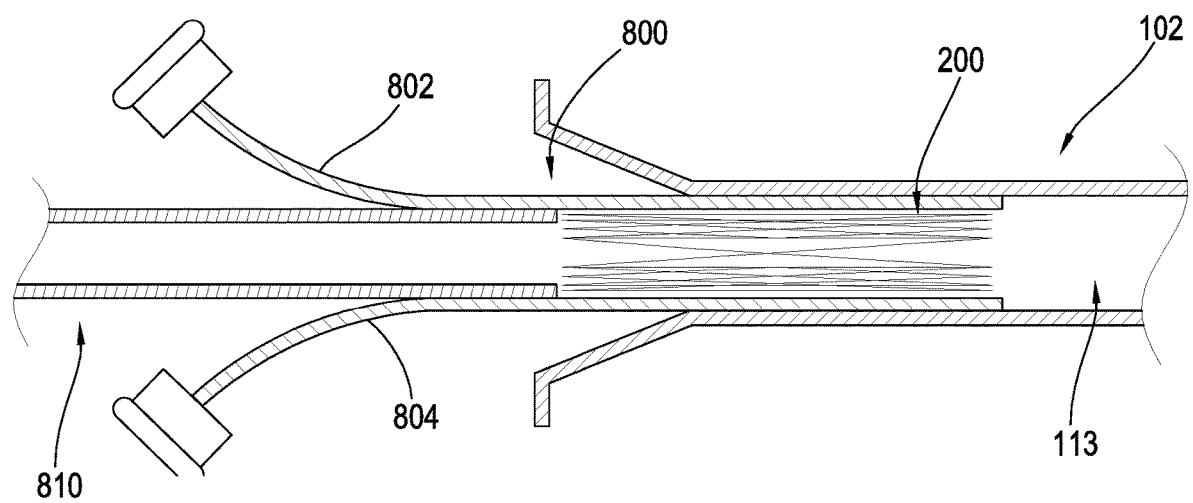
FIG. 8a illustrates a cross-sectional view of a portion of a delivery system having stent graft preloaded within a peel-away sheath and inserted into a delivery sheath.

FIG. 8a illustrates a portion of delivery system that is capable of delivering a stent graft, such as one of the exemplary stent grafts or delivery systems illustrated herein. As illustrated, stent graft 200 may be positioned within a peel-away sheath 800 that comprises a first portion 802 and a second portion 804. The first and second portions 802, 804 are separable (e.g., splittable) from one another so as to expose the stent graft. Preferably, peel-away sheath 800 retains stent graft 200 at the end of a pusher 810, and peel-away sheath 800 is sized and configured for insertion into the proximal opening of lumen 113 of sheath 102. After insertion of peel-away sheath 800, stent graft 200, and the distal end of pusher 810 into lumen 113, the first and second portions 802, 804 of peel-away sheath 800 may be separated from one another and removed from lumen 113. Pusher 810 may then be used to push stent graft 200 through lumen 113 and to the target location within the body of the patient. Additionally, stent graft 200 could be advanced over a wire guide.

Figure 8B:
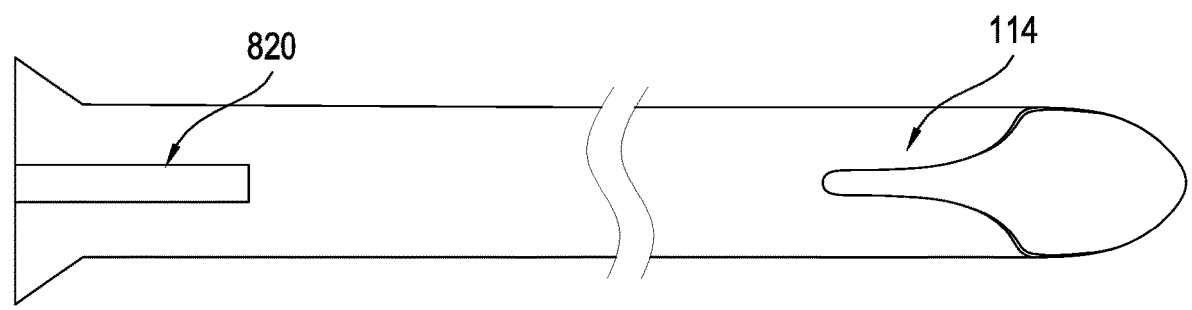
FIG. 8b illustrates a top view of a sheath.

FIG. 8b illustrates a sheath having an external marker 820 positioned along the proximal end of the sheath, such as on a handle of the sheath. External marker 820 is aligned with a side aperture, such as slot 114, that is positioned at the distal end region of the sheath. External marker therefore allows a medical professional to know the orientation of the side aperture when the distal end region of the sheath is positioned within the body of a patient.

Figure 8C:
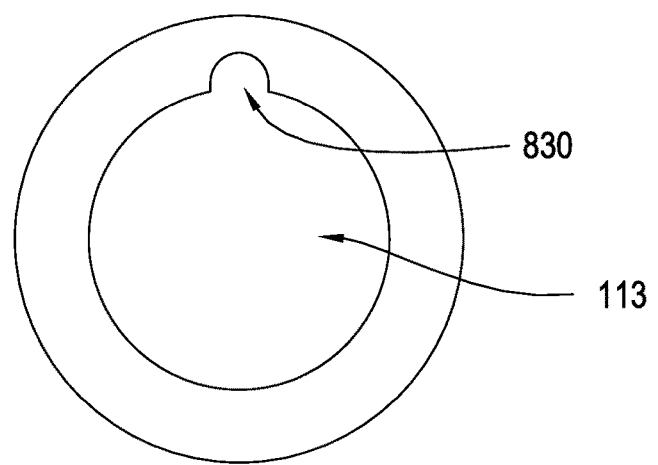
FIG. 8c illustrates a cross-sectional view of a sheath.

FIG. 8c illustrates a cross-sectional view of a sheath having a groove 830 arranged to receive an aligning member. Groove 830 preferably aligns with and/or terminates at a side aperture (e.g., slot 114) in the distal end region of the sheath. Additionally, groove 830 can align with an external marker, such as external marker 820, positioned on the handle and/or proximal end region of the sheath. As a stent graft is advanced through lumen 113 of the sheath, the aligning member that is coupled to (e.g., slidably or fixedly coupled) or integrally formed with the stent graft, tracks groove 830 and prevents rotation of the stent graft within lumen 113. This arrangement can therefore maintain alignment of the stent graft with the sheath during advancement of the stent graft through the lumen of the sheath.

Figure 9A:
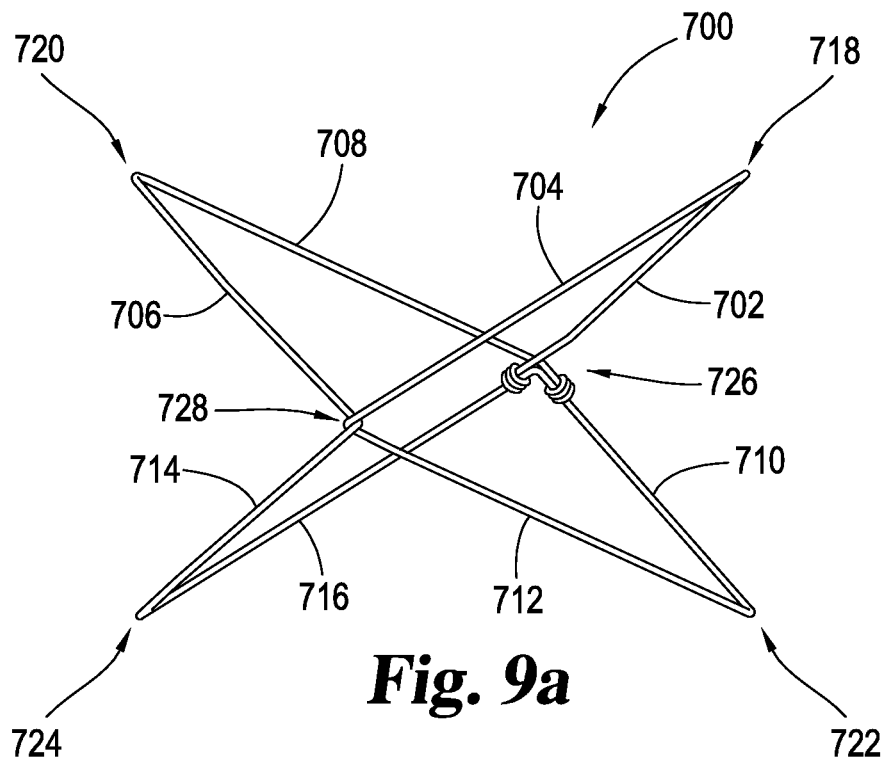
FIG. 9a illustrates a perspective view of a supporting structure for a stent graft.
Figure 9B:
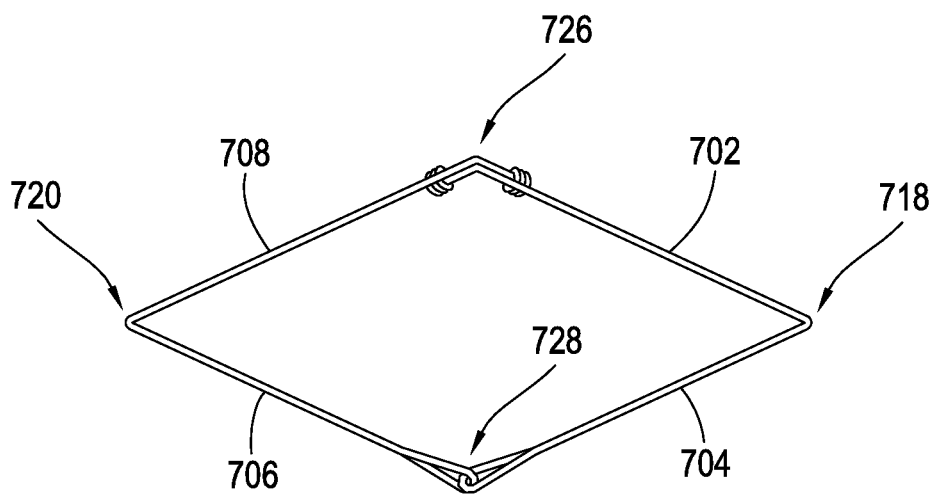
Figure 9C:
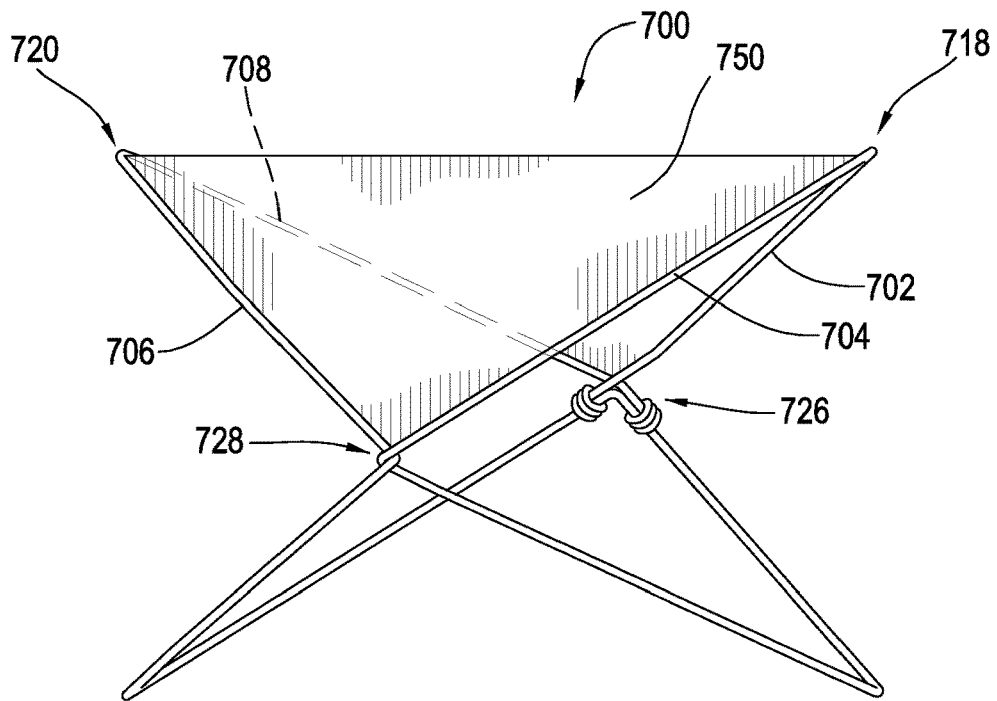
FIG. 9c illustrates the supporting structure of FIG. 9a with a covering material, so as to form a stent graft.

FIGS. 9a, 9b and 9c illustrate a frame or supporting structure 700 of a stent graft suitable for closing an opening of an aneurysm. In some instances, supporting structure 700 comprises an elongate member such as a single, continuous wire portion that is bent into an expandable configuration. For example, an elongate member may be bent so as to form a plurality of struts, such as struts 702, 704, 706, 708, 710, 712, 714 and 716, with the struts connected by bends 718, 720, 722 and 724. Adjacent bends can be connected at bend junctions 726, 728. Preferably, supporting structure 700 is arranged to self-expand when released from within a lumen 113 of a sheath 102.

FIG. 9c illustrates the supporting structure 700 having a covering material 750 extending across a portion thereof. For example, covering material 750 may extend along struts 702, 704, 706 and 708 and between bends 718, 720 so that the covering material forms a covering across a top portion of supporting structure 700.

Figure 9D:
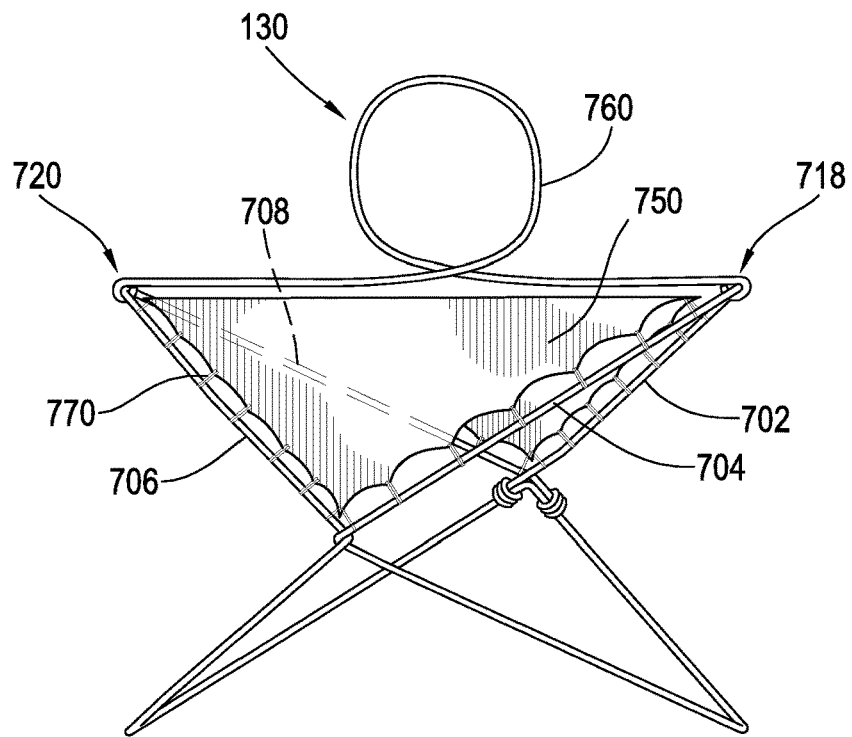
FIG. 9d illustrates a perspective view of an alternative embodiment of the stent graft illustrated in FIGS. 9a-9c, the stent graft further comprising an aligning member.

FIG. 9d illustrates a supporting structure 700 having an aligning member 130 integrally formed or attached thereto. For example, aligning member 130 may comprise a wire 760 extending from bend 718 to bend 720 and forming atraumatic loop across a central portion thereof. FIG. 9d also illustrates that covering material 750 may be attached to portions of supporting structure 700, such as struts, by one or more sutures 770.

Figure 10:
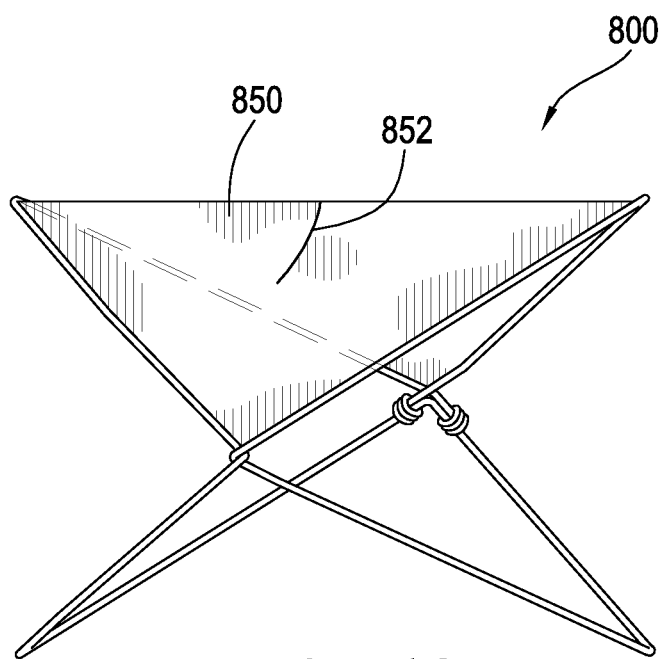
FIG. 10 illustrates a perspective view of another stent graft arrangement.

FIG. 10 illustrates a stent graft arrangement in which the supporting structure is constructed of a single, continuous wire and is arranged so that a path extending from the area within the stent graft through the patch is free of struts. For example, the stent graft may comprise a supporting structure 800 having a covering material 850 extending across a portion thereof. Covering material 850 may define a closable opening 852 (e.g., a slit) arranged to receive a wire guide. For example, supporting structure 800 and covering material 850 may be arranged for sliding advancement over a portion of a wire guide positioned within slit 852. In some exemplary methods of deploying a stent graft, a supporting structure and covering material may be advanced over a wire guide that has a portion positioned within an aneurysm or vessel target for closure. The closable opening in the covering material may be similar or the same as that illustrated and described with respect to FIGS. 7a and 7b and elsewhere in this application.

Figure 11A:
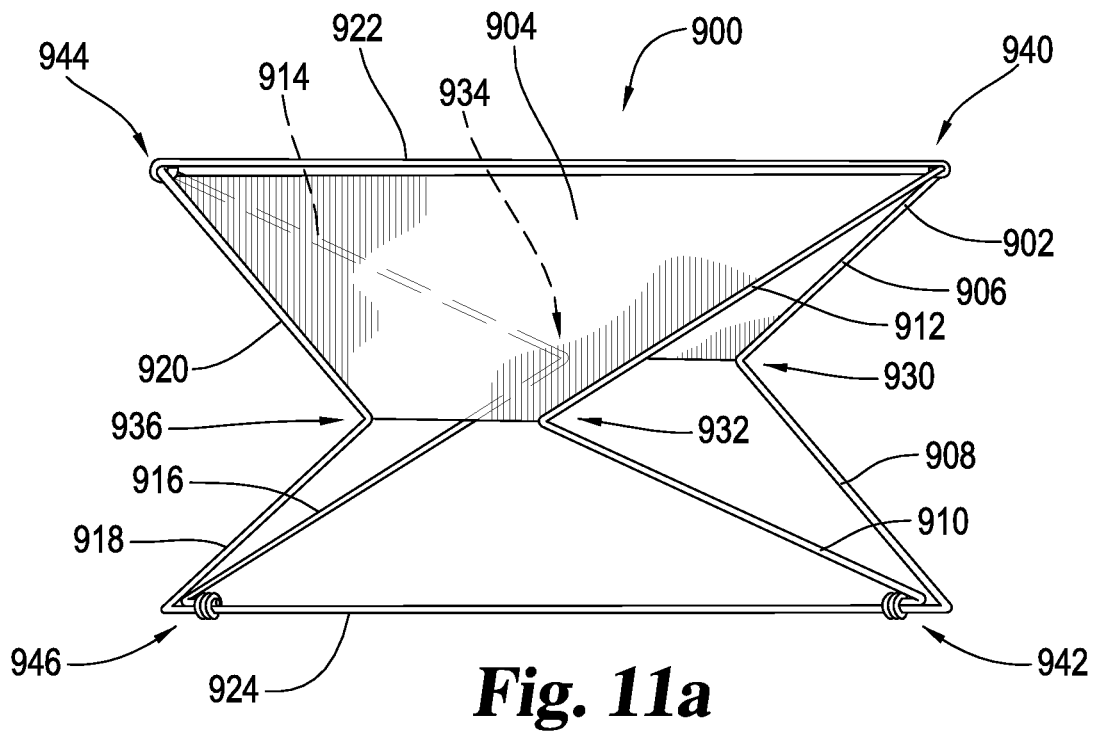
FIG. 11a illustrates a perspective view of another stent graft embodiment.
Figure 11B:
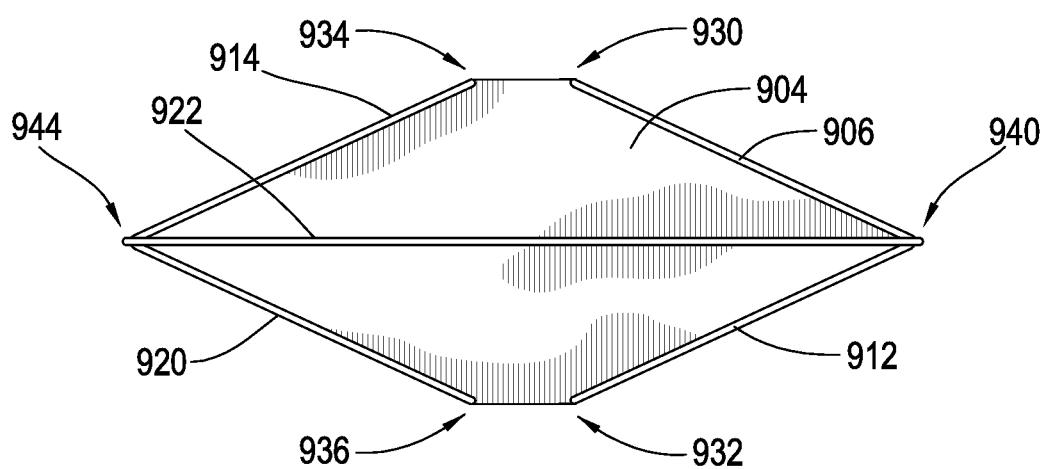

FIGS. 11a and 11b illustrate another embodiment of a stent graft 900 comprising supporting structure 902 and a covering material 904. Stent graft 900 has a greater resistance to compression along a longitudinal axis than the embodiment illustrated in FIGS. 9a-9c and maintains the same device length before and after expansion. As illustrated in FIGS. 11a and 11b, supporting structure 902 of stent graft 900 comprises struts 906, 908, 910 and 912 forming a z-stent arrangement at one end of the stent graft 900 and struts 914, 916, 918 and 920 forming a second z-stent arrangement at an opposing end of the stent graft 900. As described with regards to the supporting structure embodiments described above, portions of supporting structure 902 may be formed from one or more elongate members. For example, a single elongate member may be bent at bends 930 and/or 932. Similarly, a single elongate member may form the z-stent arrangement at the opposing end, being bent at bends 934, 936. The two z-stents of supporting structure 902 may be coupled to one another by a top strut 922 and a bottom strut 924, coupling first and second z-stents at junctions 940 and 944 along a top portion, and junctions 942, 946 along a bottom portion of the stent graft 900. Top and bottom struts 922 and 924 prevent the stent graft from changing length before and after deployment.

Figure 12A:
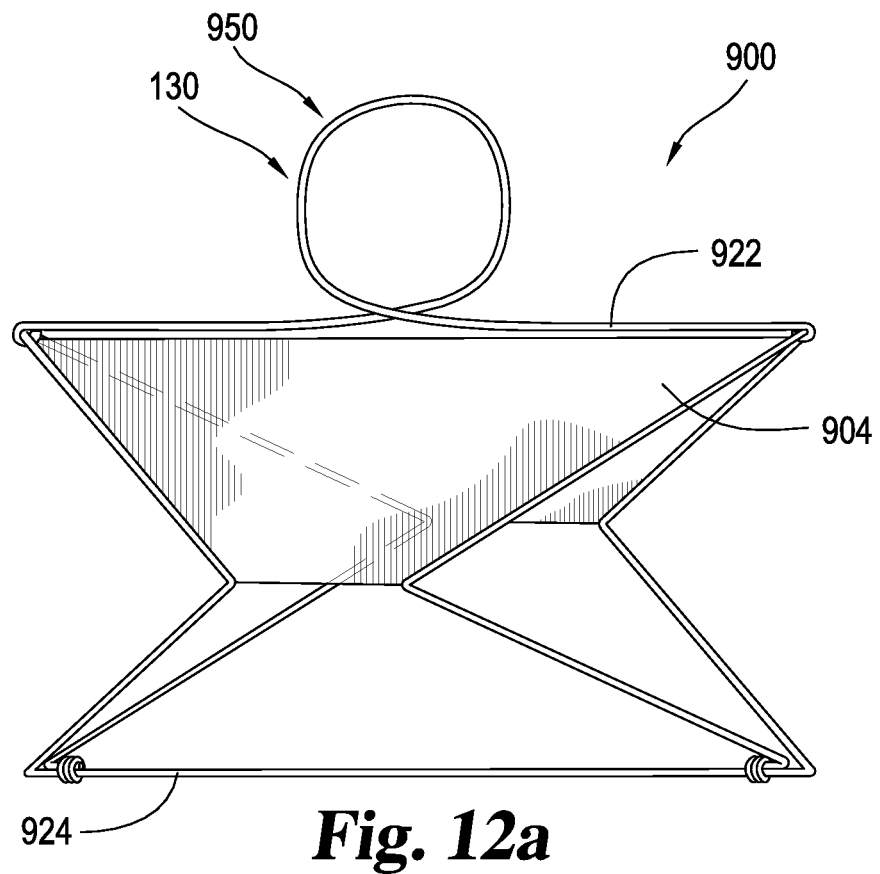
FIG. 12a illustrates a perspective view of a stent graft embodiment having an aligning member attached thereto.
Figure 12B:
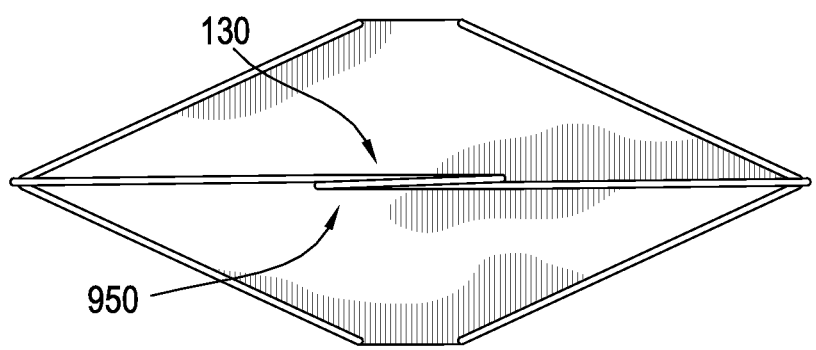

FIGS. 12a and 12b illustrate a variation of the stent graft 900 illustrated in FIGS. 11a and 11b. In FIGS. 12a and 12b, top strut 922 of stent graft 900 forms an atraumatic loop 950 arranged to function as the aligning member 130 for stent graft 900. Like bottom strut 924 in the above embodiment, bottom strut 924 prevents the stent graft from changing length before and after deployment. Additionally, covering material 904 may define a slit, such as one of those illustrated and described in FIGS. 7a, 7b, and 10. The slit can be arranged to receive a wire guide and allow the slidable movement of the covering material over the wire guide so that the covering material may be placed over the opening of a target aneurysm in which a distal portion of the wire guide is positioned.

Figure 13:
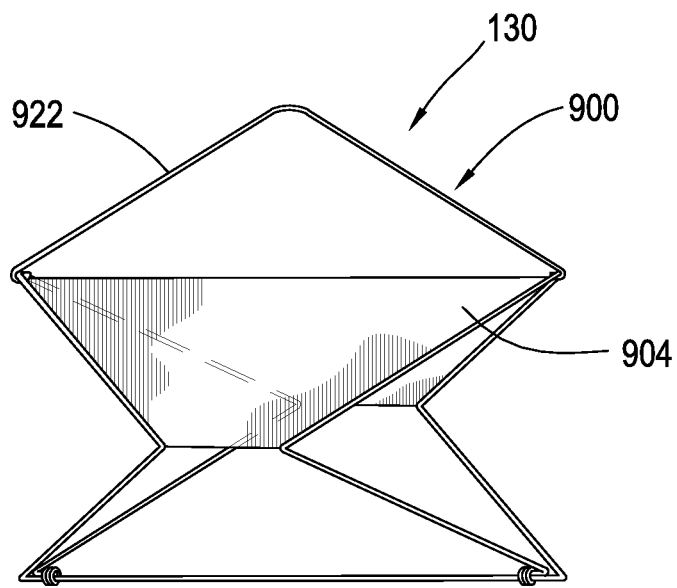
FIG. 13 illustrates an embodiment of a stent graft comprising an aligning member.
Figure 14:
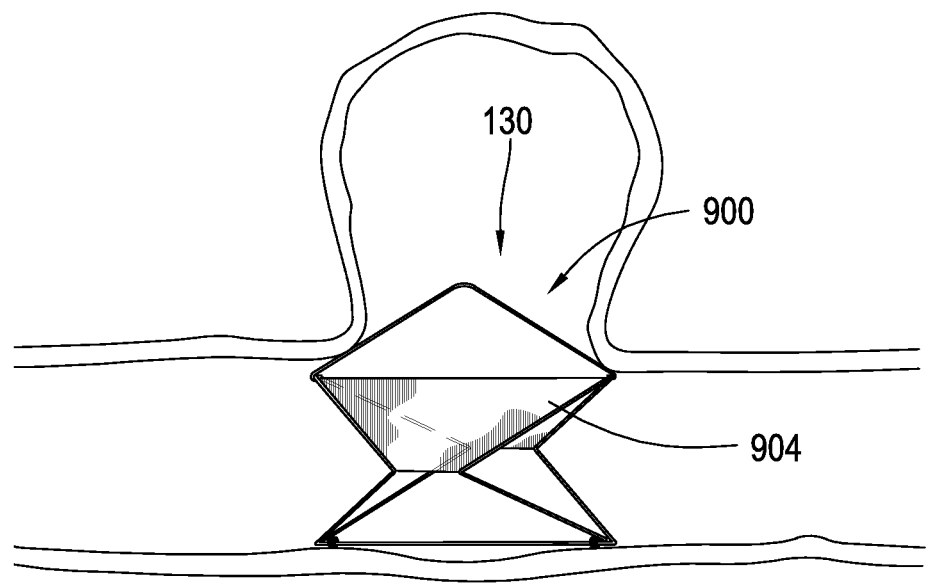
FIG. 14 illustrates the embodiment of FIG. 13 positioned within the vasculature of a patient and blocking the mouth of an opening of an aneurysm.

FIGS. 13 and 14 illustrate another embodiment of stent graft 900 comprising an aligning member. In this embodiment, aligning member 130 comprises top strut 922 bent into a triangular configuration. FIG. 14 illustrates a stent-graft, such as the embodiment of FIG. 13, positioned within a vessel of a patient, with the aligning member 130 extending into the aneurysm and aligning the covering material 904 with the mouth of the aneurysm so as to at least partially occlude and/or close the mouth of the aneurysm. Advantageously, the covering material of the stent graft can sufficiently resist blood flow into the aneurysm so as to decrease the pressure within the aneurysm and/or prevent blood flow into the aneurysm.

As will be appreciated by those of ordinary skill in the art, an aligning member may be positioned radially outward and/or radially inward of the covering material of the stent graft. For example, the end portions of the top strut 922 may be positioned radially inward (e.g., underneath) of the covering material with the central portion of the top strut 922, such as the atraumatic loop 950, extending through an opening in the covering material so as to have a portion that is positioned radially outward (e.g., above) of the outer surface of the covering material. In some embodiments, the aligning member may be positioned substantially underneath or substantially above the covering material.

Figure 15A:
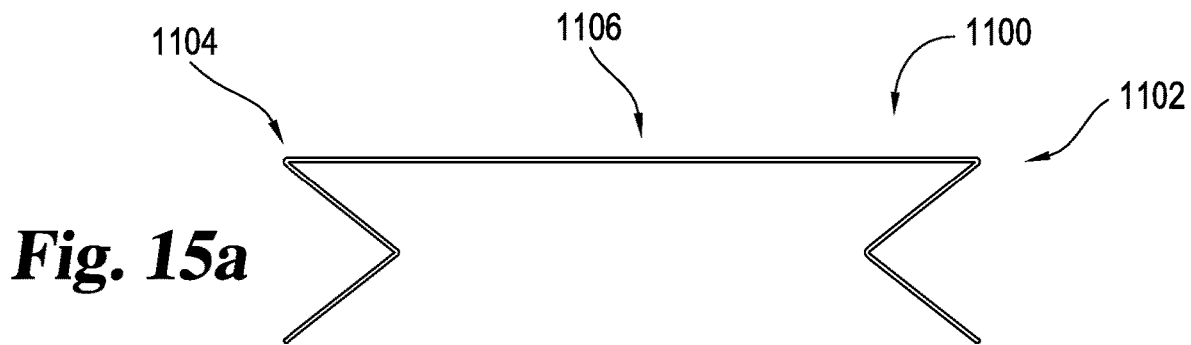
Figure 15B:
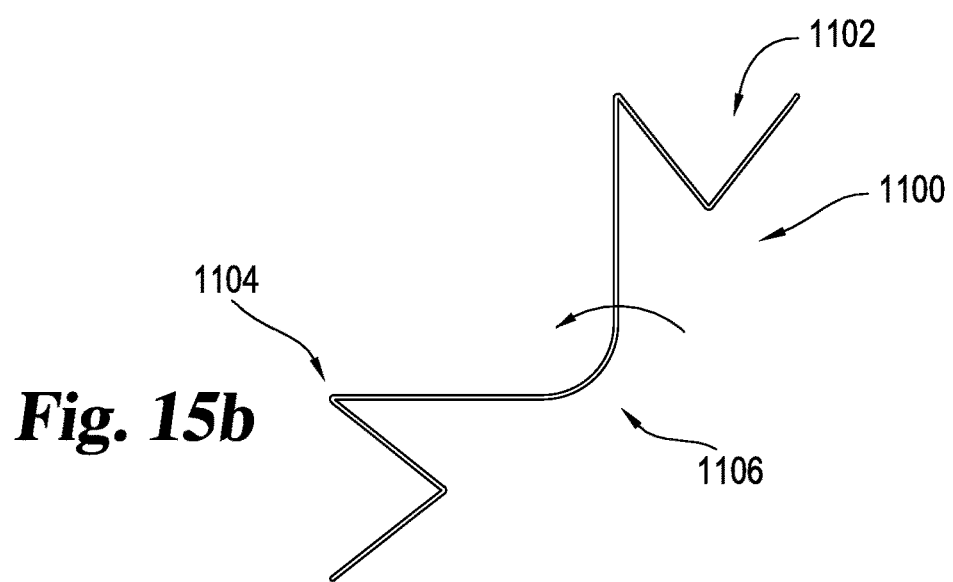
Figure 15C:
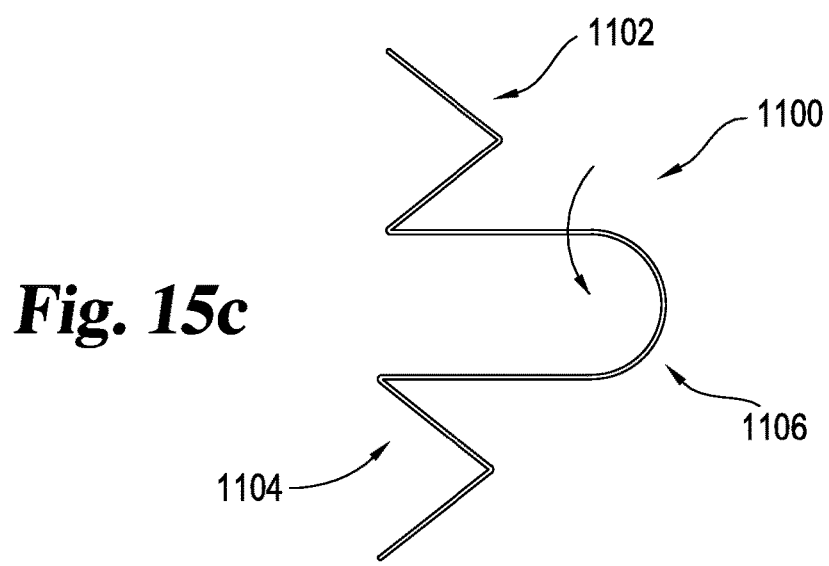
Figure 17:
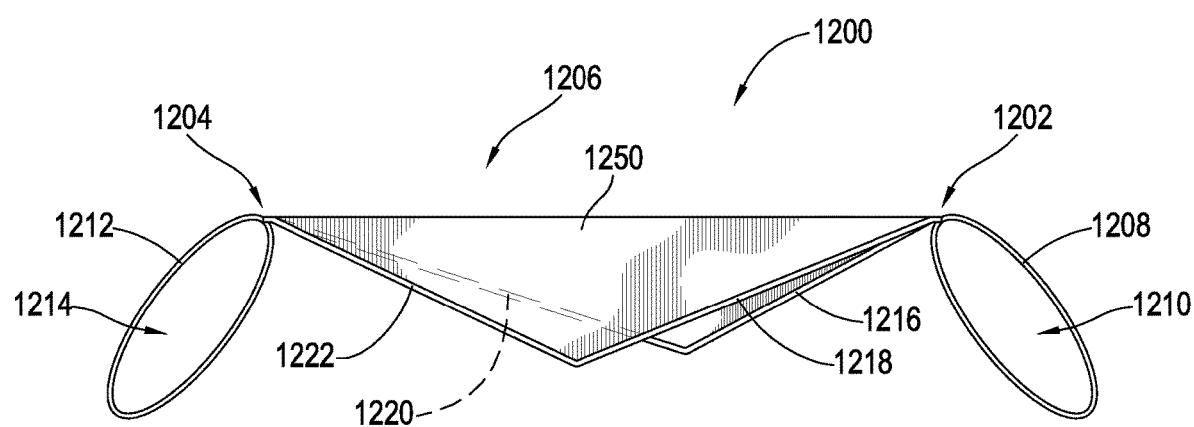
FIG. 17 illustrates a perspective view of another exemplary stent graft.
Figure 18:
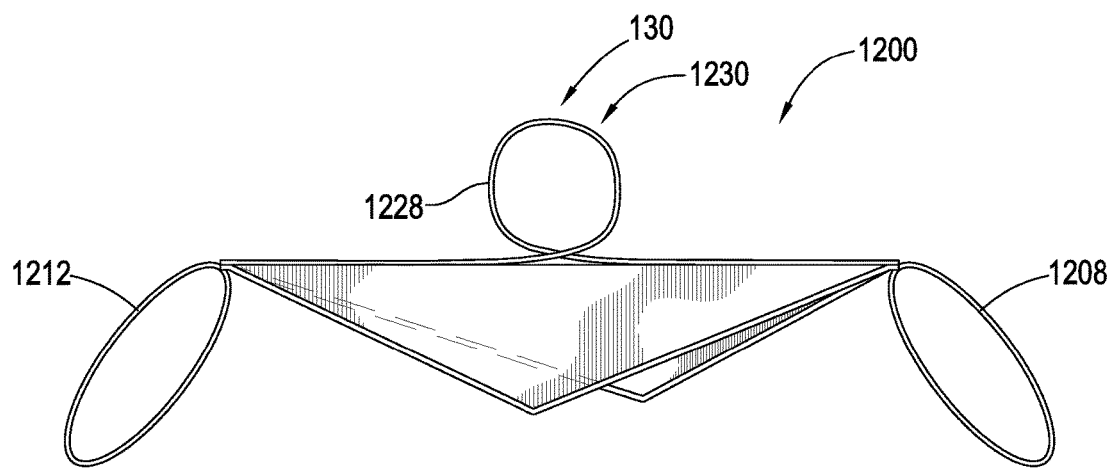
FIG. 18 illustrates a perspective view of the embodiment illustrated in FIG. 17 further comprising an aligning member.
Figure 19:
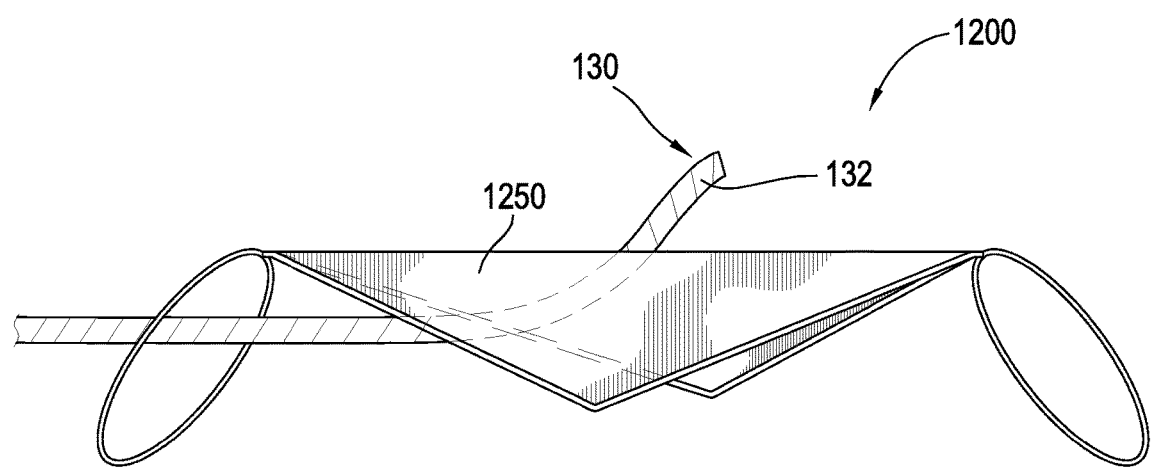
FIG. 19 illustrates a perspective view of the stent graft embodiment illustrated in FIG. 17 with a wire guide extending through the covering material.

FIGS. 15a-15f illustrate one method of forming a frame for a stent graft suitable for closing the mouth of an aneurysm. In FIG. 15a, frame 1100 comprises a distal end region 1102, a proximal end region 1104 and a central region 1106 extending between distal end region 1102 and proximal end region 1104. To form an atraumatic loop 1108 suitable to function as an aligning member 130, distal end region 1102 of frame 1100 is bent upwards towards proximal end region 1104, as illustrated in FIG. 15b. As distal end region 1102 is bent towards proximal end region 1104, central region 1106 forms a loop arrangement, shown in FIGS. 15c-15d, which is closed upon completion of a full rotation by distal end region 1102 around central region 1106. FIG. 16 illustrates a top plan view of frame 1100 formed using the method illustrated in FIGS. 15a-15f.

FIGS. 17-20 illustrate additional embodiments of a stent graft 1200 arranged for closing the mouth of an aneurysm. Stent graft 1200 can comprise a distal end region 1202, a proximal end region 1204, and a central region 1206 extending between distal end region 1202 and proximal end region 1204. Positioned at distal end region 1202 is wire member 1208 forming a loop configuration that defines an opening 1210 arranged to permit unobstructed flow of fluid through the lumen of a vessel when stent graft 1200 is deployed. Alternatively or additionally, opening 1210 defined by the loop configuration can be arranged to receive a carrier member for delivery of stent graft 1200. Similarly, positioned at proximal end region 1204 is a wire member 1212 forming a loop configuration defining an opening 1214 similar to that of wire member 1208 and opening 1210. Central region 1206 of stent graft 1200 comprises struts 1216, 1218, 1220 and 122 arranged to extend a covering material 1250 across central region 1206 of stent graft 1200.

In some instances, stent graft 1200 comprises a wire member 1228 extending from distal end region 1202 to proximal end region 1204 and forming an atraumatic loop 1230 in central region 1206. In some embodiments, it is preferred that the atraumatic loop 1230 formed by wire member 1228 is positioned over covering material 1250, so that the atraumatic loop 1230 of wire member 1228 can serve as an aligning member 130 to align covering material 1250 with the mouth of an aneurysm. Alternatively or additionally, stent graft 1200 may use a wire guide 132 as an aligning member 130, the wire guide 132 extending through an opening defined by covering material 1250 and into an aneurysm so as to align covering material 1250 of stent graft 1200 with the mouth of the aneurysm (illustrated in FIG. 19).

Figure 20:
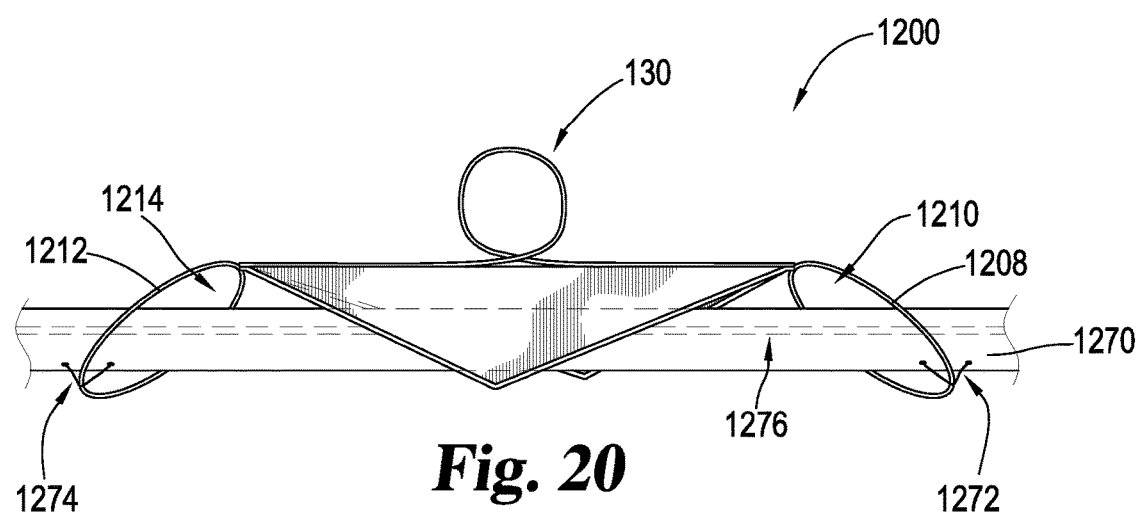
FIG. 20 illustrates a perspective view of the exemplary stent graft illustrated in FIG. 18 positioned on a carrier member for delivery within the vasculature of patient.

FIG. 20 illustrates an exemplary arrangement in which a stent graft, such as stent graft 1200, is positioned on a carrier member 1270 arranged for delivering stent graft 1200 to a target location within the body of a patient. For example, carrier member 1270 may comprise an elongate body such as a catheter arranged for positioning through openings 1210 and 1214 defined by wire members 1208 and 1212 of stent graft 1200. In some instances, carrier member 1270 includes a distal trigger wire 1272 coupled to wire member 1208 near the distal end region 1202 of the stent graft 1200. Similarly, carrier member 1270 may include a proximal trigger wire 1274 coupled to wire member 1212 at proximal end region 1204 of stent graft 1200 so that stent graft 1200 may be stretched along a longitudinal axis by trigger wires 1272 and 1274 to decrease the profile of stent graft 1200. As will be appreciated by those of ordinary skill in the art, carrier member 1270 may comprise one or more trigger wire lumens 1276 arranged to receive one or more of the trigger wires 1272, 1274 for operation of one or more of the trigger wires 1272, 1274 at the proximal end of the carrier member 1270 located outside the body of the patient of carrier member 1270.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The following numbered clauses set out specific embodiments that may be useful in understanding the present invention:

1. A system for delivering a stent graft useful for closing a mouth of an aneurysm in a vessel of a patient, comprising:
   a delivery member, a stent graft, and an aligning member;

said stent graft having a supporting structure expandable between a first configuration arranged for delivery of said stent graft with the delivery member and a second configuration arranged for deployment in a vessel;

said stent graft having a covering material extending along a portion of said stent graft; and said aligning member coupled to said stent graft and extending from an area of said stent graft covered by said covering material.

2. The system of clause 1, wherein:
said delivery member comprises a sheath having a distal end region, a proximal end region, and a sidewall extending between said distal and proximal end regions;

said sidewall defining a lumen extending along a length of said sheath and a side aperture extending through said sidewall and communicating with said lumen;

said side aperture arranged to slidably receive said aligning member; and said stent graft slidably positioned within said lumen.

3. The system of clause 2, wherein:
said side aperture having a portion positioned proximally of said distal end region of said sheath.

4. The system of clause 3, wherein:
said side aperture comprises a slot extending along a length of said sheath.

5. The system of clause 4, wherein:
said slot comprises a distal slot end and a proximal slot end and tapers along a length of said slot from said distal slot end to said proximal slot end.

6. The system of any one of clauses 3-5, wherein:
said aligning member is arranged to extend from said side aperture beyond said sidewall of said sheath so as to enter the mouth of the aneurysm.

7. The system of clause 1, wherein:
said stent graft is positioned around said delivery member.

8. The system of any preceding clause, wherein:
said covering material extends across only a portion of said supporting structure.

9. The system of any preceding clause, wherein:
said aligning member is arranged to align at least a portion of said delivery member with the mouth of the aneurysm.

10. The system of any preceding clause, wherein:
said stent graft is positioned on said delivery member in a predetermined alignment.

11. The system of any preceding clause, wherein:
said aligning member is arranged to align at least a portion of said stent graft with the mouth of the aneurysm.

12. The system of any preceding clause, wherein:
said aligning member is arranged to align said covering material of said stent graft with the mouth of the aneurysm.

13. The system of any one of clauses 3-6 or any one of clauses 8-11 when dependent thereof, wherein:
said covering material of said stent graft is aligned with said side aperture of said sheath when said stent graft is positioned within said lumen.

14. The system of any preceding clause, wherein:
said aligning member and said stent graft are slidably coupled so that said stent graft can slide along a length of said aligning member.

15. The system of any preceding clause, wherein:
said aligning member and said stent graft are coupled so that said stent graft follows said aligning member when said stent graft expands between said first and second configurations.

16. The system of any preceding clause, wherein:
said stent graft has the same length in said first configuration and said second configuration.

17. The system of any preceding clause, wherein:
said aligning member comprises a wire guide slidably extending through a portion of said stent graft.

18. The system of clause 17, wherein:
said aligning member extends through an opening in said covering material.

19. The system of clause 18, wherein:
said opening comprises separable, overlapping portions of said covering material.

20. The system of any one of clauses 17-19, wherein:
said delivery member and said wire guide are arranged to rotate at least a portion of said delivery member within the vessel of the patient so as to align said covering material of said stent graft with the mouth of the aneurysm.

21. The system of any one of clauses 1-13, wherein:
said aligning member is fixedly coupled to said stent graft and is arranged to extend away from said stent graft.

22. The system of clause 21, wherein:
said aligning member is coupled to said supporting structure.

23. The system of any one of clauses 21-22, wherein:
said aligning member comprises a wire.

24. The system of clause 23, wherein:
said wire forms an atraumatic loop.

25. The system of any one of clauses 21-24, wherein:
said aligning member is self-extending.

26. The system of any preceding clause, wherein:
said aligning member is arranged to prevent a misaligning movement of said stent graft within the vessel of the patient while said supporting structure expands into said second configuration.

27. A stent graft useful for closing a mouth of an aneurysm, comprising:
a supporting structure, a covering material, and an aligning member;

said supporting structure expandable between a first configuration and a second configuration;

said supporting structure defining a lumen in said second configuration and having said covering material extending along a length thereof and sized and configured to close the mouth of the aneurysm; and said aligning member fixedly coupled to said supporting structure, said aligning member arranged to extend away from said supporting structure.

28. The stent graft of clause 27, wherein:
said aligning member is arranged to extend away from said supporting structure in said first configuration.

29. The stent graft of clause 27, wherein:
said aligning member is arranged to extend away from said supporting structure and said lumen in said second configuration when said aligning member is aligned with an opening in a vessel wall adjacent to the stent graft.

30. The stent graft of any one of clauses 27-29, wherein:
said aligning member comprises a wire.

31. The stent graft of clause 30, wherein:
said wire forms an atraumatic loop.

32. The stent graft of any one of clauses 27-31, wherein:
said aligning member is self-extending.

33. The stent graft of any one of clauses 27-32, wherein:
said aligning member is arranged to align said stent graft with the mouth of the aneurysm prior to expansion of said supporting structure between said first and second configurations.

34. The stent graft of any one of clauses 27-34, wherein:
said aligning member is arranged to maintain alignment during expansion of said supporting structure between said first and second configurations.

35. The stent graft of any one of clauses 27-34, further comprising:
  a splitable sheath retaining said stent graft in said first configuration.
36. The stent graft of any one of clauses 27-35, wherein:
  said covering material comprises an opening arranged to slidably receive a wire guide.
37. The stent graft of clause 36, wherein:
  said opening comprises separable, overlapping portions of said covering material.
38. A device for deploying a stent within the vasculature of a patient, comprising:
  a sheath having a distal end region, a proximal end region, and a sidewall extending between said distal and proximal end regions;
  said sidewall defining a lumen extending along a length of said sheath and a side aperture extending through said sidewall and communicating with said lumen;
  said side aperture having a portion positioned proximally of said distal end region of said sheath;
  wherein said sheath is arranged to retain a stent for delivery within the vasculature of the patient; and
  wherein said side aperture is arranged to slidably receive an aligning member.
39. The device clause 38, wherein:
  said side aperture comprises a slot extending along a length of said sheath.
40. The device of clause 39, wherein:
  said slot comprises a distal slot end and a proximal slot end and tapers along a length of said slot from said distal slot end to said proximal slot end.
41. The device of any one of clauses 38-40, wherein:
  said lumen is arranged to retain the stent.
42. The device of any one of clauses 38-41, wherein:
  said side aperture is arranged to slidably receive an aligning member comprising a wire guide.
43. The device of any one of clauses 38-42, wherein:
  said lumen is arranged to slidably receive an aligning member comprising a wire guide.
44. The device of any one of clauses 38-41, wherein:
  said side aperture is arranged to slidably receive an aligning member fixedly coupled to a stent graft positioned within said lumen.
45. The device of any one of clauses 38-41 and 44, wherein:
  said side aperture is arranged to slidably receive an aligning member comprising a wire fixedly coupled to a stent graft positioned with said lumen.
46. The device of any one of clauses 38-45, wherein:
  said portion of said sheath comprising said side aperture is rotatably coupled to said proximal end of said sheath.
47. The device of any one of clauses 38-46, wherein:
  said side aperture is arranged to slidably receive an aligning member extending in a direction transverse to said sheath.

The invention claimed is:

1. A system for delivering a stent graft within vasculature of a patient, comprising:
  a delivery member, a stent graft, and an aligning member;
  said stent graft having a supporting structure expandable between a first configuration arranged for delivery of said stent graft with the delivery member and a second configuration arranged for deployment in a vessel;
  said stent graft having a covering material extending along a portion of said stent graft;
  said aligning member coupled to said stent graft and extending from an area of said stent graft covered by said covering material;
  wherein said delivery member comprises a sheath having a distal end region, a proximal end region, and a sidewall extending between said distal and proximal end regions;
  said sidewall defining a lumen extending along a length of said sheath and a side aperture extending through said sidewall and communicating with said lumen;
  said side aperture arranged to slidably receive said aligning member;
  said stent graft slidably positioned within said lumen;
  said side aperture having a portion positioned proximally of said distal end region of said sheath;
  wherein said side aperture is a slot extending along a length of said sheath;
  wherein said slot comprises a distal slot end and a proximal slot end and tapers inwardly along a length of said slot starting from said distal slot end and extending towards said proximal slot end;
  wherein a first portion of said sidewall extends along a first side of said lumen and a second portion of said sidewall extends along a second side of said lumen opposite said first side;
  wherein said distal slot end is defined by said first portion of said sidewall; and
  wherein a distal surface of said second portion is distal of said distal slot end and curves in a concave direction towards said proximal end region.

2. The system of claim 1, wherein:
  said aligning member comprises a wire guide slidably extending through a portion of said stent graft.

3. The system of claim 2, wherein:
  said aligning member extends through an opening in said covering material.

4. The system of claim 3, wherein:
  said opening is defined by separable, overlapping portions of said covering material; and
  wherein said overlapping portions include a first overlapping edge portion extending over a second overlapping edge portion and said aligning member extends between said first and second overlapping edge portions.

5. The system of claim 2, wherein:
  said delivery member and said wire guide are arranged to rotate at least a portion of said delivery member within the vessel of the patient so as to align said covering material of said stent graft with an opening in a vessel wall.

6. The device of claim 2, comprising a wire guide diverting member positioned within the lumen of the sheath, the wire guide diverting member comprising an arcuate surface arranged to divert portions of the wire guide through a side of the stent graft.

7. The system of claim 1, wherein:
  said aligning member is fixedly coupled to said stent graft and is arranged to extend away from said stent graft.

8. The device of claim 1, wherein the slot is tapered along the entire length extending from the distal slot end to the proximal slot end.

9. The device of claim 1, wherein the sheath has a rounded distal tip.

10. The device of claim 1, wherein said distal slot end is at least twice as wide as said proximal slot end.

11. A device for deploying a stent within the vasculature of a patient, comprising:
  a sheath having a distal end region, a proximal end region, and a sidewall extending between said distal and proximal end regions;

said sidewall defining a lumen extending along a length of said sheath and a side aperture extending through said sidewall and communicating with said lumen;
said side aperture having a portion positioned proximally of said distal end region of said sheath;
wherein said sheath is arranged to retain a stent for delivery within the vasculature of the patient;
wherein said side aperture is arranged to slidably receive an aligning member;
wherein said side aperture is a slot extending along a length of said sheath; and
wherein said slot comprises a distal slot end and a proximal slot end and tapers inwardly along a length of said slot starting from said distal slot end and extending towards said proximal slot end;
wherein a first portion of said sidewall extends along a first side of said lumen and a second portion of said sidewall extends along a second side of said lumen opposite said first side;
wherein said distal slot end is defined by said first portion of said sidewall; and
wherein a distal surface of said second portion is distal of said distal slot end and curves in a concave direction towards said proximal end region.

12. The device of claim 11, wherein:
said side aperture is arranged to slidably receive an aligning member comprising a wire guide.

13. The device of claim 11, wherein the slot is tapered along the entire length extending from the distal slot end to the proximal slot end.

14. The device of claim 11, comprising a wire guide diverting member positioned within the lumen of the sheath, the wire guide diverting member comprising an arcuate surface arranged to divert portions of a wire guide through the slot.

15. The device of claim 11, wherein the sheath has a rounded distal tip.

16. The device of claim 11, wherein said distal slot end is at least twice as wide as said proximal slot end.

17. A device for deploying a stent within the vasculature of a patient, comprising:
a sheath having a longitudinal axis, a distal end region, a proximal end region, and a sidewall extending between said distal and proximal end regions;
said sidewall defining a lumen extending along a length of said sheath and a side aperture extending through said sidewall and communicating with said lumen;
said side aperture having a portion positioned proximally of said distal end region of said sheath;
wherein said sheath is arranged to retain a stent for delivery within the vasculature of the patient;
wherein said side aperture is arranged to slidably receive an aligning member;
wherein said slot comprises a distal slot end and a proximal slot end and tapers inwardly along a length of said slot starting from said distal slot end and extending towards said proximal slot end; and
wherein said distal slot end is at least twice as wide as said proximal slot end.

* * * * *